US011149265B2

(12) United States Patent
Ismagilov et al.

(10) Patent No.: US 11,149,265 B2
(45) Date of Patent: Oct. 19, 2021

(54) PURIFICATION AND DETECTION OF ANALYTES

(71) Applicant: CALIFORNIA INSTITUTE OF TECHNOLOGY, Pasadena, CA (US)

(72) Inventors: Rustem Ismagilov, Altadena, CA (US); Erik Jue, Pasadena, CA (US); Daan Witters, San Diego, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 402 days.

(21) Appl. No.: 16/130,810

(22) Filed: Sep. 13, 2018

(65) Prior Publication Data

US 2019/0100747 A1 Apr. 4, 2019

Related U.S. Application Data

(60) Provisional application No. 62/558,679, filed on Sep. 14, 2017.

(51) Int. Cl.
*B01L 3/00* (2006.01)
*B01L 7/00* (2006.01)
(Continued)

(52) U.S. Cl.
CPC .......... *C12N 15/1003* (2013.01); *B01L 3/508* (2013.01); *B01L 3/50851* (2013.01); *B01L 3/502753* (2013.01); *B01L 7/52* (2013.01); *C12N 15/1006* (2013.01); *C12N 15/1013* (2013.01); *C12Q 1/6806* (2013.01); *G01N 21/6428* (2013.01); *G01N 21/6456* (2013.01);

*B01L 2200/0631* (2013.01); *B01L 2200/0689* (2013.01); *B01L 2300/04* (2013.01);
(Continued)

(58) Field of Classification Search
None
See application file for complete search history.

(56) References Cited

U.S. PATENT DOCUMENTS 5,582,988 A 12/1996 Backus et al.
8,883,088 B2 11/2014 Malik et al.
(Continued)

FOREIGN PATENT DOCUMENTS

JP 2005531750 A 10/2005
JP 2006194843 A 7/2006
(Continued)

OTHER PUBLICATIONS

"Adsorption" in the Glossay. The Brownfields and Land Revitalization Technology Support Center. http://www.brownfieldstsc.org/glossay.cfm?q=1 Date captured: Jan. 16, 2009. (https://brownfieldstsc.org/glossary.cfm?q=1). 2 pages.
(Continued)

*Primary Examiner* — Holly Kipouros
(74) *Attorney, Agent, or Firm* — Steinfl + Bruno LLP

(57) ABSTRACT

A sample preparation module accepts a sample including a target analyte. The sample preparation module processes the sample through several reaction chambers and a solid phase column. Different reagents are present in the reaction chambers. The eluted analyte is then transferred to the amplification module, where it is further processed and amplified for optical analysis.

18 Claims, 22 Drawing Sheets

(51) Int. Cl.
G01N 21/64 (2006.01)
C12N 15/10 (2006.01)
C12Q 1/6806 (2018.01)

(52) U.S. Cl.
CPC . *B01L 2300/069* (2013.01); *B01L 2300/0672* (2013.01); *B01L 2300/18* (2013.01); *B01L 2400/0605* (2013.01)

(56) References Cited

U.S. PATENT DOCUMENTS

| | | | |
|---|---|---|---|
| 9,415,392 | B2 | 8/2016 | Ismagilov et al. |
| 9,518,291 | B2 | 12/2016 | Malik et al. |
| 9,561,505 | B2 | 2/2017 | Malik et al. |
| 9,803,237 | B2 | 10/2017 | Ismagilov et al. |
| 9,822,356 | B2 | 11/2017 | Ismagilov et al. |
| 10,252,264 | B2 | 4/2019 | Shen et al. |
| 2004/0191923 | A1 | 9/2004 | Tomasso et al. |
| 2005/0169801 | A1 | 8/2005 | Fogel et al. |
| 2006/0159586 | A1 | 7/2006 | Sasaki et al. |
| 2006/0183216 | A1* | 8/2006 | Handique ............ B01L 3/52 435/287.1 |
| 2008/0138884 | A1 | 6/2008 | Takeshita et al. |
| 2008/0293931 | A1 | 11/2008 | Dunbar et al. |
| 2010/0028204 | A1 | 2/2010 | Lee et al. |
| 2012/0077969 | A1 | 3/2012 | Petzel et al. |
| 2012/0184725 | A1 | 7/2012 | Forman et al. |
| 2014/0039177 | A1 | 2/2014 | Nelson et al. |
| 2015/0184149 | A1 | 7/2015 | Jiang et al. |
| 2016/0346781 | A1 | 12/2016 | Shen et al. |
| 2017/0037394 | A1 | 2/2017 | Chua et al. |
| 2019/0078080 | A1 | 3/2019 | Ismagilov |

FOREIGN PATENT DOCUMENTS

| | | |
|---|---|---|
| WO | 2016/105508 A2 | 6/2016 |
| WO | 2019/35800 A2 | 7/2019 |
| WO | 2019/135801 A2 | 7/2019 |

OTHER PUBLICATIONS

1-Undecanol. GESTIS Substance Database downloaded from <http://gestis.itrust.de/nxt/gateway.dll/gestis_en/000000.xml?f=templates&fn=default.htm&vid=gestiseng:sdbeng> on Apr. 17, 2020. 2 Pages.
3M Fluorinert™ FC-40 Electronic Liquid. Mat Web Material Property Data. Dowloaded from <http://www.matweb.com/search/datasheettext.aspx?matguid=2072a809f9ca4d 529b1d136660736f81> on Apr. 17, 2020. 2 Pages.
ABD El-Aal, A. A., et al., Comparative study of five methods for DNA extraction from whole blood sampes. *International Journal of Health Science3*, pp. 285-, 2010. 4 Pages.
Alaeddini, R., Forensic implications of PCR inhibition—A review. Forensic science international: Genetics 6, 297-305, doi: 10.1016/j.fsigen.2011.08.006, pp. 297-305, 2012. 11 Pages.
Ali, N., et al., Current Nucleic Acid Extraction Methods and Their Implications to Point-of-Care Diagnostics. *BioMed research international2017*, 9306564, doi: 10.1155/2017/9306564, 2017. 13 Pages.
Arkles, B., et al., Silicone Fluids; Stable, Inert Media, *Gelest, Inc*, 2013. 34 Pages.
Barton, Allan FM, et al., Alcohols with Water in Solubility Data Series vol. 15. Pergamon Press, 1984, 457 Pages.
Bergallo, M. et al. Evaluation of six methods for extraction and purification of viral DNA from urine and serum samples. *The new microbiologica29*, 111-119, 2006, 10 pages.
Berry, S. M., et al., One-step purification of nucleic acid for gene expression analysis via Immiscible Filtration Assisted by Surface Tension (IFAST). Lab on a chip 11, 1747-1753, doi: 10.1039/c1lc00004g, 2011, 7 pages.
Biava, M. et al. Evaluation of a rapid and sensitive RT-qPCR assay for the detection of Ebola Virus. *J. Virol. Methods252*, 70-74, dol: 10.1016/j.jviromet.2017.11.009, 2018. 7 Pages.

Boesenberg-Smith, K.A., et al., Assessment of DNA yield and purity: an overlooked detail of PCR troubleshooting. *Clin. Microbiol. News. 34*, No. 1, 1-6, Jan. 1, 2012. 6 Pages.
Bustin, S. A., et al. Quantitative real-time RT-PCR—a perspective. J. Mol. Endocrinol. 34, 597-601, doi:10.1677/jme.1.01755, 2005. 5 pages.
Chacon-Coretes, D., et al., Methods for extracting genomic DNA from whole blood samples: current perspectives. *Journal of Biorepository Science for Applied Medicine2014*, 1-9, 2014, 9 pages.
Craw, P. et al., isothermal nucleic acid amplification technologies for point-of-care diagnostics: a critical review. *Lab on a chip12*, 2469-2486, doi:10.1039/c2lc40100b, 2012. 18 Pages.
Crotchfelt, K. A., et al., Detection of Neisseria gonorrhoeae and Chlamydia trachomatis in genitourinary specimens from men and women by a coamplification PCR assay. J. Clin. Microbial. 35, 1536-1540, 1997, 5 pages.
Day, E., et al., Digital PCR strategies in the development and analysis of molecular biomarkers for personalized medicine. Methods59, 101-107, 2013, 7 pages.
Demeke, T., et al., Influence of DNA extraction methods, PCR inhibitors and quantification methods on real-time PCR assay of biotechnology-derived traits. Anal. Bioanal. Chem. 396, 1977-1990, doi: 10. 1007 /s00216-009-3150-9, 2010. 14 pages.
Francois, P., et al. Robustness of a loop-mediated isothermal amplification reaction for diagnostic applications. FEMS Immunol. Med. Microbial. 62, 41-48, doi:10.1111/j.1574-695X.2011.00785.x, 2011, 8 pages.
Gielis, E. M. et al., Cell-Free DNA: An Upcoming Biomarker in Transplantation. Am. J. Transplant: 15, 2541-2551, doi:10.1111/ajt. 13387, 2015. 11 Pages.
Goldberg, C. S., et al., Environmental DNA as a new method for early detection of New Zealand mudsnails (Potamopyrgus antipodarum). Freshwater Science 32, 792-800, Jun. 18, 2013, 9 Pages.
Goto, M., et al., Colorimetric detection of loop-mediated isothermal amplification reaction by using hydroxy naphthol blue. Bio Techniques 46, 167-172, doi:10.2144/000113072, 2009, 4 pages.
Hu, Q., et al., A comparison of four methods for PCR inhibitor removal. Forensic science international: Genetics 16, 94-97, doi:10.1016/j,fsigen .2014.12.001, 2015. 6 pages.
Huggett, J.F., et al., Differential susceptibility of PCR reactions to inhibitors: an important and unrecognised phenomenon. BMC Res. Notes 1, 70, doi:10.1186/1756-0500-1-70, Aug. 28, 2008, 9 pages.
International Preliminary Report on Patentability (Chapter I) for International Application No. PCT/US2018/051201 filed on Sep. 14, 2018 on behalf of California Institute of Technology dated Mar. 26, 2020, 8 pages.
International Preliminary Report on Patentability for International Application No. PCT/US2018/050919 filed on Sep. 13, 2018 on behalf of California Institute of Technology dated Mar. 26, 2020 8 pages.
International Preliminary Report on Patentability for International Application No. PCT/US2018/050919 filed Sep. 13, 2018 on behalf of California Institute of Technology. dated Mar. 17, 2020. 7 Pages.
Kamau, E., et al., Multiplex qPCR for detection and absolute quantification of malaria. PLoS One 8, e71539, doi: 10.1371/journal.pone.0071539, Aug. 2013, 9 pages.
Kaneko, H., et al., Tolerance of loop-mediated isothermal amplification to a culture medium and biological substances. *J. Biochem. Biophys. Methods70*, 499-501, doi:10.1016/j.jbbm.2006.08.008, 2007,5 Pages.
Klein, D., Quantification using real-time PCR technology: applications and limitations. Trends Mol. Med.8, 257-260, published online: May 8, 2002, 4 pages.
Kogovsek, P., et al., Rapid loop-mediated isothermal amplification assays for grapevine yellows phyto plasmas on crude leaf-vein homogenate has the same performance as qPCR. Eur. J. Plant Pathol. 148, 75-84, 2017, 10 pages.
Kuehnelt, D.M., et al., Quantitative PCR of bacteriophage lambda DNA using a second-generation thermocycler. PCR Methods Appl. 3, 369-371, 1994, 4 pages.

(56) References Cited

OTHER PUBLICATIONS

Lee, S. R., et al., Rapid one step detection of pathogenic bacteria in urine with sexually transmitted disease (STD) and prostatitis patient by multiplex PCR assay (mPCR). J. Microbial.45, n. 5, 453-459,2007. 7 Pages.
Mahony, J., et al. Urine specimens from pregnant and nonpregnant women inhibitory to amplification of Chlamydia trachomatis nucleic acid by PCR, ligase chain reaction, and transcription-mediated amplification: identification of urinary substances associated with inhibition and removal of inhibitory activity. J. Clin . Microbial. 36, n. 11, 3122-3126, 1998. 5 pages.
Mason, W.J., et al., Multiplex PCR protocol for the diagnosis of staphylococcal infection. J. Clin. Microbial. 39, n. 9, 3332-3338, doi: 10.1128/jcm.39.9.33323338.2001, 2001. 7 Pages.
Matsuda, K., et al., Sensitive quantitative detection of commensal bacteria by rRNA-targeted reverse transcription-PCR. Appl. Environ. Microbial. 73, n.1, 32-39, doi:10.1128/aem.01224-06, Jan. 2007. 8 pages.
Nixon, G. et al. Comparative study of sensitivity, linearity, and resistance to inhibition of digital and nondigital polymerase chain reaction and loop mediated isothermal amplification assays for quantification of human cyto megalovirus. Anal. Chem. 86, 4387-4394, doi:10.1021/ac500208w, 2014.8 Pages.
Nolan, T., et al., SPUD: a quantitative PCR assay for the detection of inhibitors in nucleic acid preparations. Anal. Biochem. 351, 308-310, doi: 10.1016/j.ab.2006.01.051, 2006. 3 Pages.
Notomi, T. et al., Loop-mediated isothermal amplification of DNA. Nucleic Acids Res. 28, E63, doi: 10.1093/nar/28.12.e63, 2000, 7 pages.
Opel, K. L., et al., A study of PCR inhibition mechanisms using real time PCR. J. Forensic Sci. 55, 25-33, doi:10.1111/j.1556-4029.2009. 01245.x, 2010, 10 pages.
Peist, R., et al., PCR inhibitors in plant DNA preparations. Qiagen news 3, 7-9, 2001, 4 pages.
Price, C. W.,et al., Nucleic acid extraction techniques and application to the microchip, Lab on a chip 9, 2484-2494, doi:10.1039/b907652m, 2009. 11 Pages.
Priye, A., et al., A smartphone-based diagnostic platform for rapid detection of Zika, chikungunya, and dengue viruses. Sci. Rep. 7, 44778, doi:10.1038/srep44778, 2017. 11 pages.
Qiu, J., et al., Development of a Real-Time Polymerase Chain Reaction Method to Measure Ligation Efficiency. Journal of Experimental Microbiology and Immunology, 2015, .7 pages.
Radstrom, P., et al., Strategies for overcoming PCR inhibition. CSH protocols 2008, pdb.top20, doi: 10.1101/pdb.top20, 2008, 12 pages.
Rossen, L., et al., Inhibition of PCR by components of food samples, microbial diagnostic assays and DNA-extraction solutions. Int. J. Food Microbiol. 17, 37-45, doi:10.1016/0168-1605(92)90017-w, 1992, 11 pages.
Rudi, K., et al., Different length (DL) qPCR for quantification of cell killing by UV-induced DNA damage. int. J. Env. Res. Public Health 7, 3376-3381, doi: 10.3390/ijerph7093376, 2010, 6 pages.
Schoepp, N.G., et al., Rapid pathogen-specific phenotypic antibiotic susceptibility testing using digital LAMP quantification in clinical samples. Sci. Transl. Med. 9, eaal3693, doi:10.1126/scitranslmed. aal369 , Oct. 4, 2017. 13 pages.
Schrader, C., et al., PCR inhibitors—occurrence, properties and removal. J. Appl. Microbial. 113, 1014-1026, doi:10.1111/j.1365-2672.2012.05384.x, 2012. .13 pages.
Simbolo, M., et al. DNA qualification workflow for next generation sequencing of histo pathological samples. PLoS One 8, e62692, doi:10.1371/journal.pone.0062692, Jun. 6, 2013. 8 pages.
SR, K., PCR Technique with its Application. Research & Reviews: Journal of Microbiology and Biotechnology 4, 1-12, Feb.-Mar. 2015. 13 pages.
Sriworarat, C., et al., Development of loop mediated isothermal amplification (LAMP) for simple detection of Leishmania infection. Parasites & vectors 8, 591, doi: 10.1186/s13071-015-1202-x, 2015, 8 pages.
Sur, K., et al., Immiscible phase nucleic acid purification eliminates PCR inhibitors with a single pass of paramagnetic particles through a hydrophobic liquid. The Journal of molecular diagnostics 12, 620-628, doi: 10.2353/jmoldx.2010.090190, 2010, 9 Pages.
Tanner, N. A., et al., Loop-mediated isothermal amplification for detection of nucleic acids. Curr. Protoc. Mol. Biol. 105, Unit 15.14., doi:10.1002/0471142727.mb1514s105, 2014, 14 pages.
Tebbe, C. C., et al., Interference of humic acids and DNA extracted directly from soil in detection and transformation of recombinant DNA from bacteria and a yeast. Appl. Environ. Microbiol. 59, 2657-2665, 1993, 9 pages.
Valones, M. A. et al., Principles and applications of polymerase chain reaction in medical diagnostic fields: a review. Braz, J. Microbial. 40, 1-11, doi:10.1590/s1517-83822009000100001, 2009, 11 pages.
Wilson, I. G. Inhibition and facilitation of nucleic acid amplification. Appl. Environ. Microbial. 63, No. 10, pp. 3741-3751, 1997, 11 pages.
Yager, P., et al., Point-of-care diagnostics for global health. Annu. Rev. Biomed. Eng. 10, 107-144, doi:10.1146/annurev.bioeng.10. 061807.160524, 2008. 40 pages.
Yamakazi, W., et al,, Development of a loop-mediated isothermal amplification assay for sensitive and rapid detection of Vibrio parahaemolyticus. BMC Microbial. 8, 163, doi:10.1186/1471-2180-8-163, Sep. 30, 2008, 7 pages.
"Adsorption" in the Glossary. The Brownfields and Land Revitalization Technology Support Center, Retrieved Dec. 19, 2009. web. archive.org/web/20091219063871/http://www.brownfieldstsc.org/glossary.cfm. 2 pages.
Non-Final Office Action for U.S. Appl. No. 16/132,235 filed Sep. 14, 2018 on behalf of California Institute of Technology dated Jan. 12, 2021. 22 pages.
Crini, Chapter 1—"Sorption processes and pollution: conventional and non-conventional sorbents for pollutant removal", Presses universitaires de Franche-Comte, 2010, p. 34-37, ISBN 9782848673042.
Witters, et al., "Autonomous and portable device for rapid sample-to-answer molecular diagnostics at the point-of-care", 2017, California Institute of Technology Pasadena CA, SlipChip Corp, Menlo Park, USA. 1 page.
International Search Report for International Application No. PCT/US2018/050919 filed Sep. 13, 2018 on behalf of California Institute of Technology. dated Aug. 2, 2019. 4 pages.
International Search Report for International Application No. PCT/US2018/051201 filed Sep. 14, 2018 on behalf of California Institute of Technology. dated Aug. 1, 2019. 4 pages.
Lee, et all, "Centrifugation-free extraction of circulating nucleic acids using immiscible liquid under vacuum pressure", Scientific Reports, (2018), 8:5467, pp. 1-11.
Written Opinion for International Application No. PCT/US2018/050919 filed Sep. 13, 2018 on behalf of California Institute of Technology. dated Aug. 2, 2019. 6 pages.
Written Opinion for International Application No. PCT/US2018/051201 filed Sep. 14, 2018 on behalf of California Institute of Technology. dated Aug. 1, 2019. 6 pages.
Jue, E., et al., "Two-phase wash to solve the ubiquitous contaminant-carryover problem in commercial nucleic-acid extraction kits", Scientific Reports, (2020) 10:1940. 16 pages.
Restriction Requirement for U.S. Appl. No. 16/132,235 filed Sep. 14, 2018 on behalf of California Institute of Technology dated Aug. 11, 2020 8 pages.

* cited by examiner

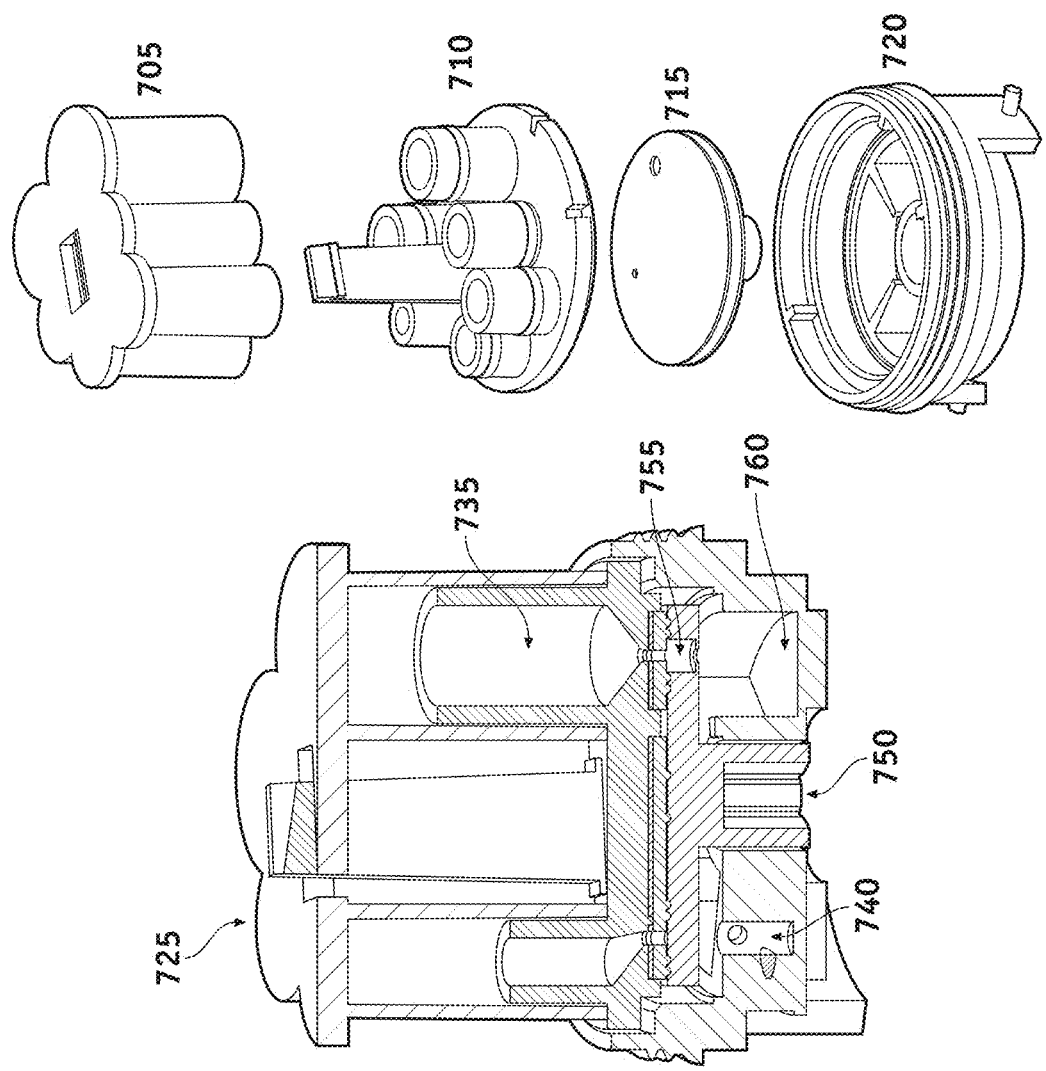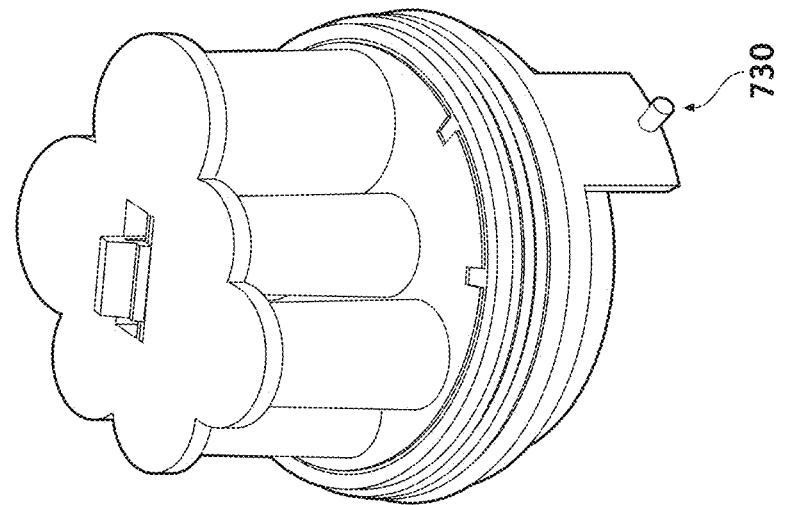
FIG. 7

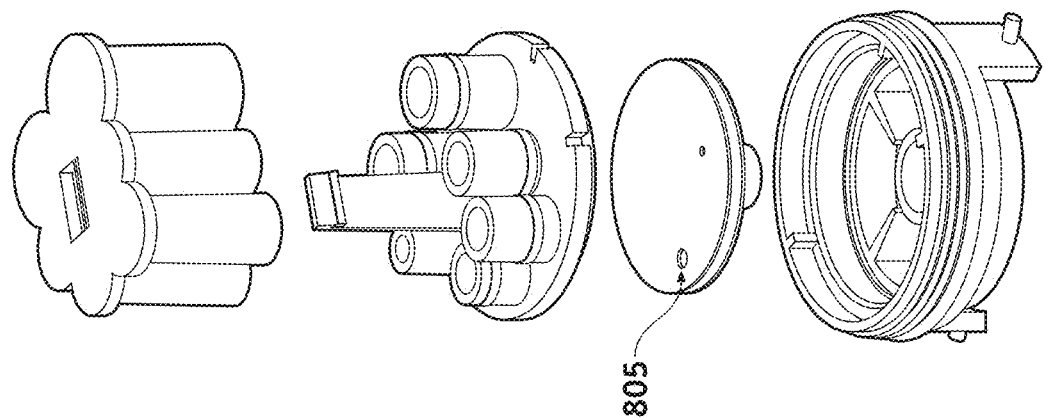
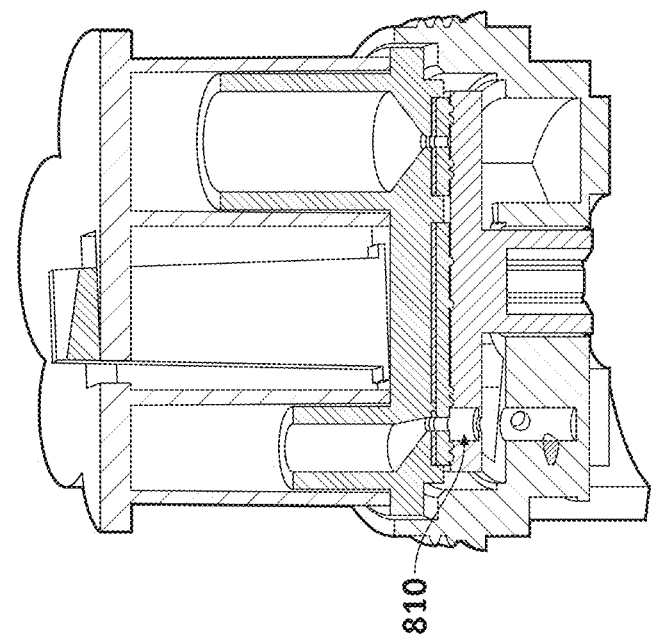
FIG. 8
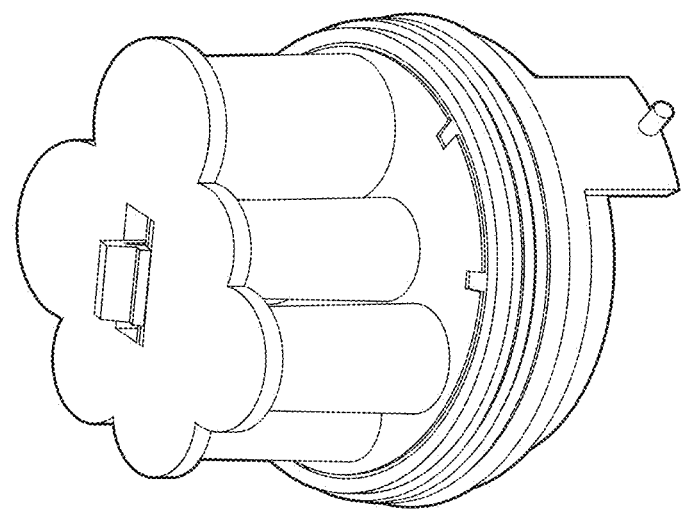

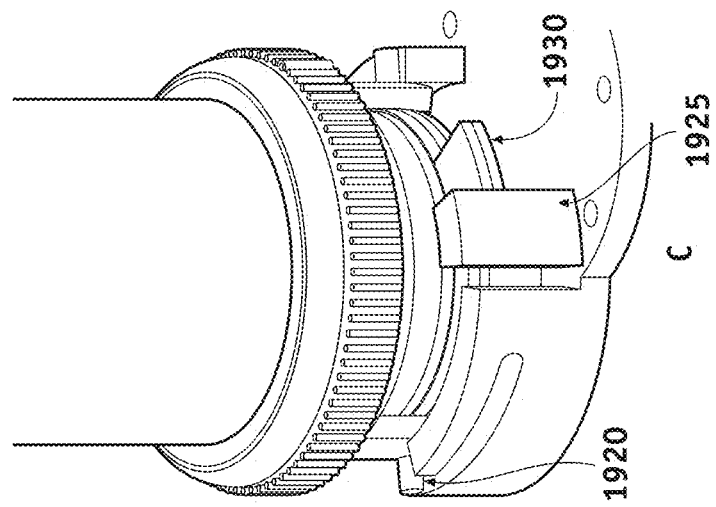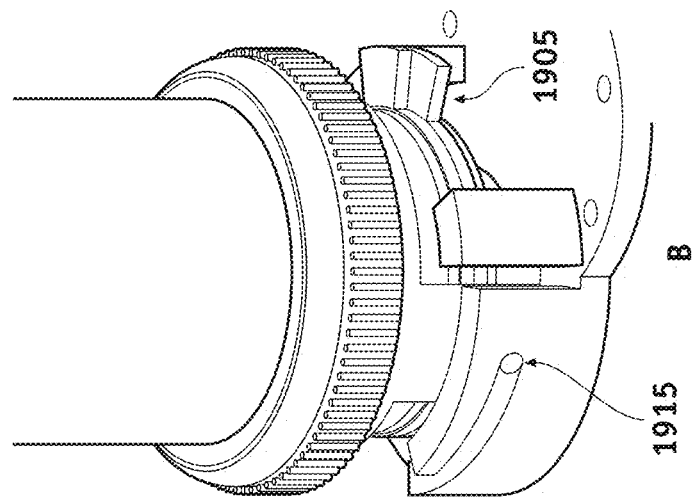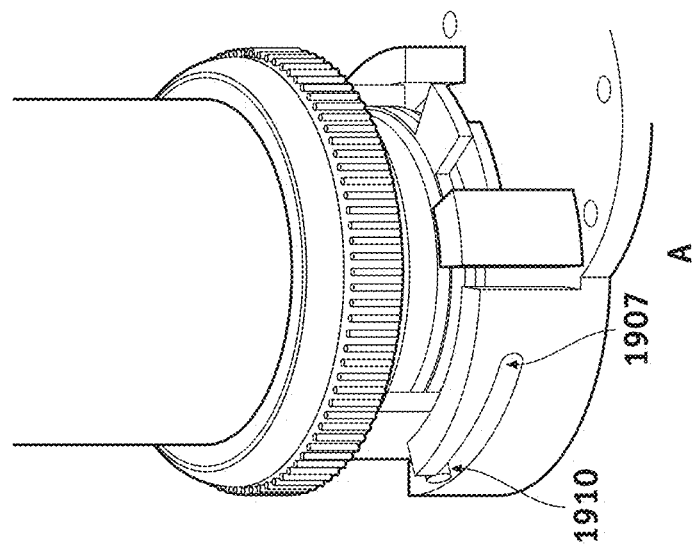
FIG. 19

PURIFICATION AND DETECTION OF ANALYTES

CROSS REFERENCE TO RELATED APPLICATIONS

The present application claims priority to U.S. Provisional Patent Application No. 62/558,679, filed on Sep. 14, 2017, and may be related to U.S. Pat. No. 9,822,356, issued on Nov. 21, 2017, U.S. Pat. No. 9,561,505, issued on Feb. 7, 2017, U.S. Pat. No. 9,518,291, issued on Dec. 13, 2016, U.S. Pat. No. 9,803,237, issued on Oct. 31, 2017, U.S. Pat. No. 9,415,392, issued on Aug. 16, 2016, and US Patent Application 20160346781, published on Dec. 1, 2016, the disclosures of all of which are incorporated herein by reference in their entirety.

STATEMENT OF INTEREST

This invention was made with government support under Grant No. HR0011-11-2-0006 awarded by DARPA. The government has certain rights in the invention.

TECHNICAL FIELD

The present disclosure relates to the detection of analytes. More particularly, it relates to the purification and detection of analytes.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIGS. 5-10 illustrate different views of an exemplary sample preparation module.

FIG. 19 illustrates the operation of the rotating section connecting the amplification device to the sample preparation device.

SUMMARY

Figure 1:
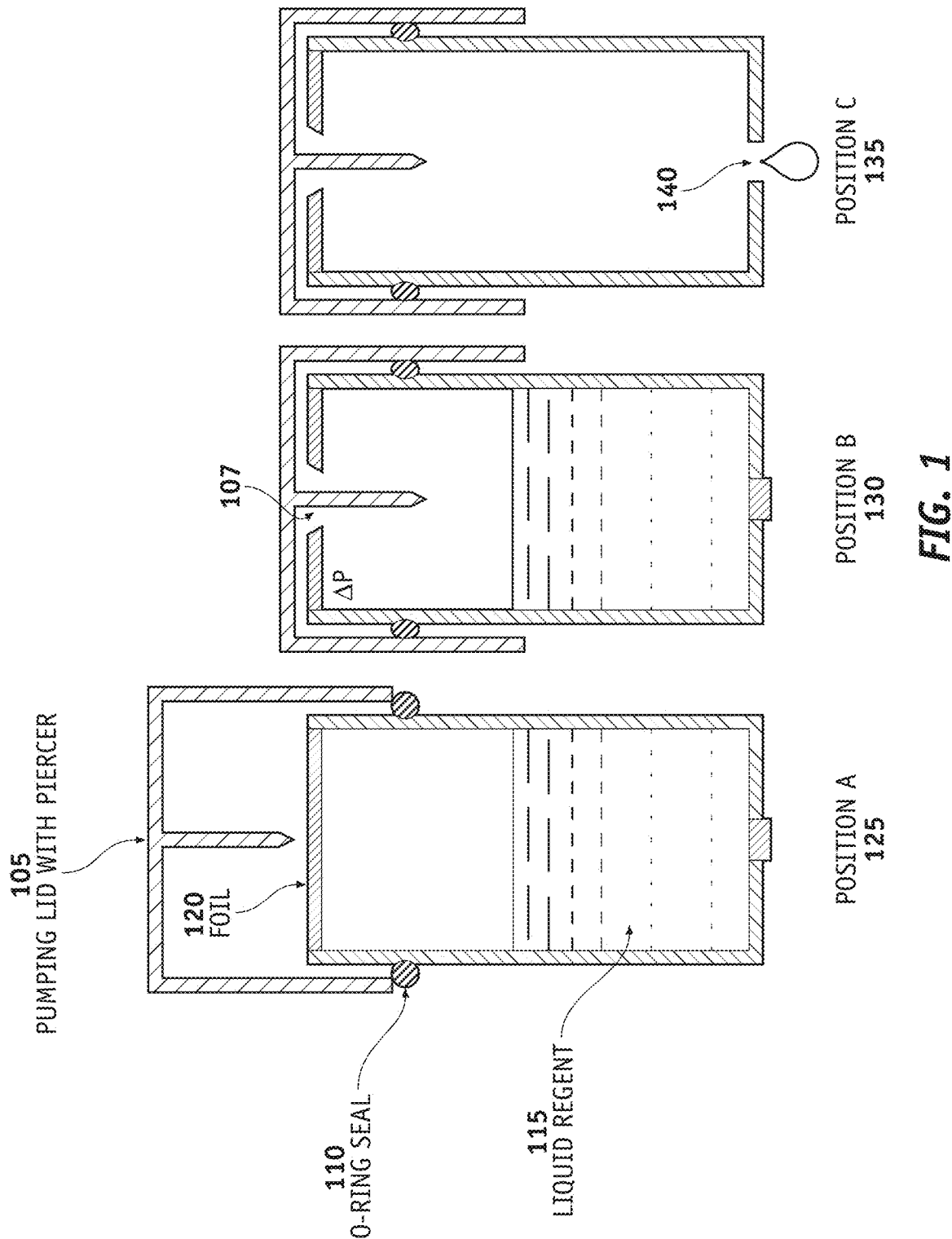
FIGS. 1-2 illustrate exemplary embodiments of pierceable membranes sealing chambers.

In a first aspect of the disclosure, a device is described, the device comprising: a plurality of chambers, each chamber of the plurality of chambers comprising a top opening, a bottom opening, and a seal; a lid configured to: seal the plurality of chambers by contacting the seal of each chamber of the plurality of chambers, and upon pushing of the lid towards the plurality of chambers, simultaneously pressurize each chamber of the plurality of chambers; a storage section comprising a plurality of receptacles; and a rotating section between the plurality of chambers and the storage section, the rotating section comprising a solid phase column, wherein the rotating section is configured to rotate to form, in sequence, a fluidic pathway between the solid phase column, the bottom opening of each chamber of the plurality of chambers, and a receptacle of the plurality of receptacles, thereby allowing flow of a pressurized fluid from a chamber of the plurality of chambers through the solid phase column into a receptacle of the plurality of receptacles.

In a second aspect of the disclosure, a device is described, the device comprising: a first plate comprising: a first fluidic channel having a first inlet and a first plurality of outlets; and a second fluidic channel having a second inlet and a second plurality of outlets; and a second plate comprising a first plurality of reaction wells and a second plurality of reaction wells, wherein: the second plate is configured to rotate, relative to the first plate, between a first position and a second position, the first position forms a fluidic pathway between each reaction well of the first plurality of reaction wells and an outlet of the first plurality of outlets, and a fluidic pathway between each reaction well of the second plurality of reaction wells and an outlet of the second plurality of outlets, and the second position fluidically isolates the first plurality of reaction wells from the first plurality of outlets, and the second plurality of reaction wells from the second plurality of outlets.

DETAILED DESCRIPTION

The present disclosure describes an autonomous device for managing fluid flow, biochemical reactions and purification of nucleic acids or other target analytes. Specific methods are described for the purification and washing of target analytes from samples. The present disclosure also describes devices for the extraction and purification of target analytes, and the amplification of nucleic acid molecules from a sample. Conventional technologies rely on centrifugation for transporting liquid solutions through a solid-phase material, for capturing the analyte, followed by wash solutions and an elution buffer. Centrifugation is not a suitable method for portable devices that want to accomplish the same process. The present disclosure describes methods for performing the purification process of target analytes, such as nucleic acids, with pressurization-based methods. Therefore, the devices of the present disclosure acquire portability through the use of pressure, which can be generated in portable devices, as a substitute of centrifugation, which requires heavier equipment and is therefore limited to a laboratory environment.

Pressurization-based methods face intricate challenges such as the difficulty of removing remnant liquid solution from the solid-phase column effectively, and effective methods for automating the process of subsequent pressure-based pumping of liquid solutions through the solid-phase column, especially on a miniaturized, portable device format. As known to the person of ordinary skill in the art, a solid-phase column is a porous matrix structure that is used to perform, capture and wash steps in the analysis of a target analyte. Molecules bind in various ways to the matrix, and liquids are able to move through the solid-phase column thanks to the gaps, or pores, within the matrix. The pores can have dimensions in the range of micrometers, e.g. a hundred micrometers or hundreds of micrometers.

The devices of the present disclosure are able to perform pressure-based methods due to a variety of techniques implemented in the portable device. For example, a force can be stored in the device, or generated in the field either manually, by the application of a mechanical force by a user (e.g. pushing on a part of the device), or automatically, by the application of a mechanical force by a motor. The reagents within a device can be dispensed through the stored force, with a timed valve control.

In some embodiments, pushing on the pumping lid of the device, either manually or by a motor, generates a "stored force". In other words, one or more compartments can be pressurized by pumping the lid. The device can have multiple independently pressurized reaction chambers. Each chamber can accommodate different sample volumes, and have its own designated pressure profile based on different parameters (sample volume, inner diameter, outer diameter, chamber height, seal height, pumping lid height, etc.)

Reagents may be stored using foil or blister packs, which break at high pressures, or are pierceable by piercers on the pumping lid. For example, the pumping lid may have a sharp point which, when the lid is pushed down, will pierce the blister pack and release the liquid. The liquid within the blister is therefore free to exit the blister and enter the device's chamber. For example, the blister can be located within the chamber. In other embodiments, instead of a blister which envelops the liquid entirely, the liquid may be contained within the chamber, with a foil on the top of the chamber. In this case, the foil is pierced in a similar manner of the blister embodiment. The foil may also be on the bottom of the chamber, or both the top and bottom. The blister pack is essentially a foil which completely surrounds the liquid.

In some embodiments, the devices of the present disclosure can incorporate a Slip-Chip with parallel dead-end filling. A Slip-Chip is a device that allows the movement of chambers relative to each other, so that the fluid within can be directed in different microfluidic pathways depending on the progression of the reactions to be performed. The reaction chambers of the devices of the present disclosure can also contain lyophilized reagents, with each chamber having independent rehydration, and droplet compartmentalization. The lyophilized reagents can be rehydrated with the same solution, without cross-over contamination. Each lyophilized reagent can contain different assays. For example, the assays may comprise a loop mediated isothermal amplification (LAMP) reaction with primers targeting different pathogen nucleic acid (NA) sequences.

The volume of the each well, or reaction chamber, determines the specific rehydration volume. The device can also incorporate a small dead-volume, after rehydrating reagents, relative to the size of the well. The dead volume is filled with the solution. For example, the dead volume may be less than 20% of the chamber's volume, or <15%, <10%, <5%, <1%, etc. In some embodiments, the dead volume is about 0.91 μL relative to a 17-μL well (this amounts to a dead volume of 5.35%).

In some embodiments, it is possible to use a base station, which is a second device to which the first device can be connected. In this case, the first device houses the reagent chambers. The sample to be analyzed is inserted in the first device, where different steps, such as lysis or different washes, can be performed. The base station enables automated heating, slipping of the Slip-Chip, and rotation of the rotating layer connecting the different chambers. For example, the base station may contain a motor that allows rotation of the device, or pushing of the pressurizing lid. The base station may contain a heater, in which case the first device does not require a heater. The base station may be larger than the first device, and therefore be less portable, but still more portable than the standard equipment found in a laboratory.

In some embodiments, rotation of the first device in one direction locks the integrated device into the base station and rotates the rotating layer containing different chambers and microfluidic pathways. Rotation in the opposite direction unlocks the integrated device and actuates the slip-feature of the Slip-Chip. Automated and integrated sample preparation and nucleic acid amplification can therefore be realized with a system comprising a device and a base station. The first device may comprise one or more of two components: a sample preparation module, and an amplification module. The sample preparation module accepts the sample to be analyzed, and prepares it for amplification. For example, the sample preparation module may purify the sample by removing some impurities. The sample preparation module may be operated as a stand-alone device or integrated with the amplification module, or integrated with the amplification module and the base station.

The amplification module carries out amplification of nucleic acids. The amplification module may be operated as a stand-alone device or integrated with the sample preparation module, or integrated with the sample preparation module and base station. The sample preparation module may be operated manually or automatically with the base station. The pre-pressurization and slip valving approach described above may be used generally for a variety of fluid handling processing including but not limited to in-vitro diagnostics, nucleic acid amplifications, immunoassays, enrichment, antibiotic discovery, antibiotic susceptibility testing, solid-phase extractions, bacterial capture, viral capture, cell capture, protein crystallization, organic chemistry, catalyst discovery, purifications.

The pierceable blister foils described above can be used for reagent storage and on-demand release of liquid reagents. FIG. 1 illustrates an exemplary embodiment of pierceable membranes sealing reaction chambers, with a pressuring lid which integrates a piercing element. The same mechanism can be used for different kinds of containers in the device, for example containing wash buffers, eluting liquids, or other reagents. In the example of FIG. 1, a chamber in a first position (125) contains a liquid reagent (115), sealed within the chamber by a foil (120). The pumping lid (105) includes a piercer (107) which can pierce the foil when the lid is pressed down, either manually or automatically with a motor. The motor may be contained within the device or in a separate, but connectable, base station. The lid can pierce the foil and at the same time pressurize the chamber. In other words, pushing the lid exerts a force on the liquid in the chamber, and the gas (e.g. air) in the chamber, and therefore increases the pressure within the chamber. The higher pressure can be used by the device to move the liquids within the different reaction chambers. An O-ring seal (110), e.g. made of rubber, seals the chamber and allows pressurization. Once the lid is pushed down, the pressure in position (130) is increased. Position (135) illustrates how the liquid can exit the chamber from the bottom opening (140). The bottom opening may be connected to microfluidic or mesofluidic pathways and to other chambers. The device can be rotated to align different microfluidic channels, thus allowing the liquids to move between chambers in a designed sequence.

Figure 2:
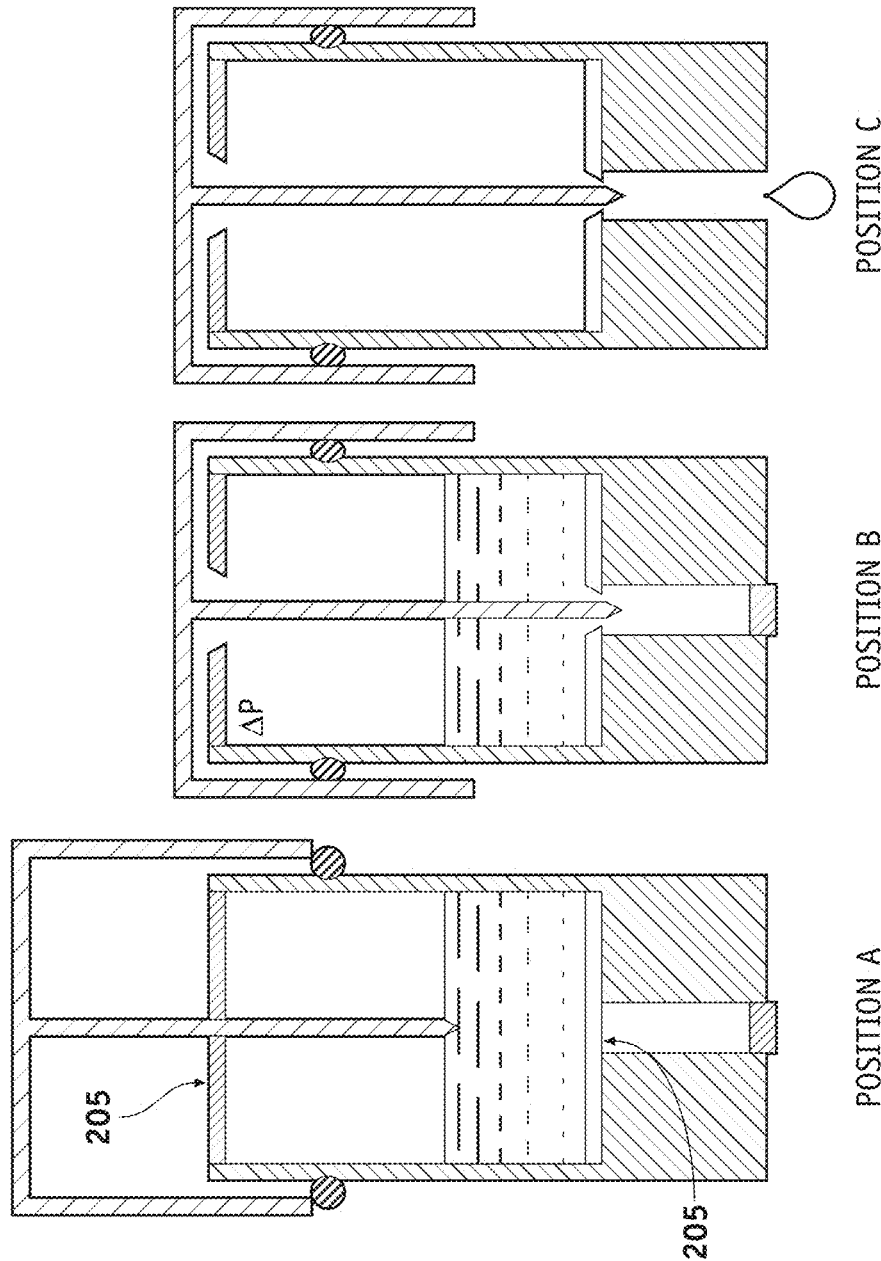

FIG. 2 illustrates a different embodiment with a piercer that is longer than the length of the chamber. This type of chamber has foils (205) on both the top and bottom, and both foils are pierced by the same piercer in the lid. The chamber works in a similar way as that of FIG. 1, including the use of pressurization and O-rings.

Figure 3:
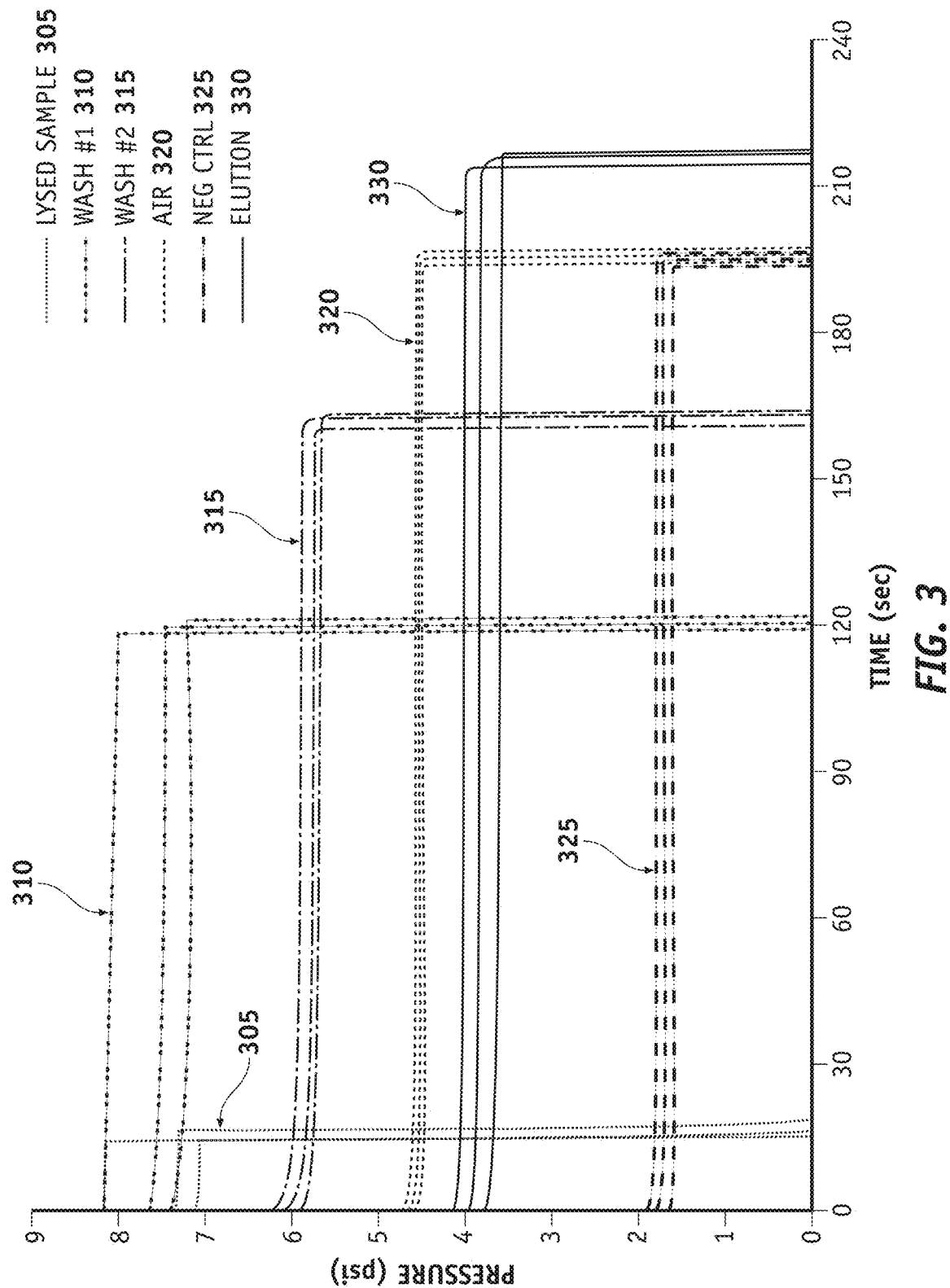
FIG. 3 illustrates pressure curves within multiple chambers.

FIG. 3 illustrates pressure curves of different chambers within a device. The pressure data was obtained by including pressure gauges in a prototype device. However, normally a device would not include pressure gauges as they are generally unnecessary to the operation of the device once the device has been properly tested and fabricated. FIG. 3 illustrates an exemplary operation of the device, with different steps as described in the following. FIG. 3 illustrates curves that all begin at a certain pressure level, and drop after a certain time. Therefore, all curves have an approximately step-wise shape, dropping from their initial pressure value to zero pressure. Each curve actually comprises three curves as the measurements were repeated for confirmation. For clarity, each label in FIG. 3 refers to each curve as a single curve even though the three curves are visible in parts of the plot. When the pressure is measured in a device containing six reagent compartments, it is possible to monitor the pressure and observe it drop when the column in the rotating layer is aligned with a particular reagent reservoir. To this end, it is possible to observe how a lysed sample, a first wash buffer, a second wash buffer, air, a negative control sample and an elution buffer are sequentially pumped through the column of a rotating layer. The number and designation of each chamber can be selected for the application.

The lysed sample curve (305) drops from about 7.5 psi to zero past the 15 seconds mark. The lysed sample curve plots the pressure values within the chamber where the lysed sample is inserted. In some embodiments, the devices of the present disclosure describe how to process a lysed sample. The sample containing the target analyte is pre-processed by lysing, and then inserted in an input chamber of the devices of the present disclosure. For example, a syringe or pipette may be used to insert the lysed sample in a first chamber.

The lysed sample is then moved (through pressurization) through the reaction chamber to a second chamber, such as a waste chamber or receptacle. In other words, the lid of the device is pressed down, and the subsequence pressure moves the lysed sample from the first chamber through the reaction chamber to the second chamber, by forming a microfluidic connection between the chambers. Each rotation or activation of the device can connect different chambers to move the liquid from one chamber to the next chamber in the reaction sequence. In the next step, the wash buffer passes through the reaction chamber into a waste chamber. The pressure in the first wash chamber (310) drops from about 8 psi to zero at the 120 s mark. The second wash pressure, in a second wash chamber, drops from 6 psi to zero at the 160 s mark.

Curve (320) plots the pressure of air in an optional air chamber; the pressure drops from just below 5 psi to zero around the 200 s mark. A negative control curve (325) shows a pressure dropping from 2 psi to zero at the 200 s mark. An elution curve (330) shows a pressure dropping from 4 psi to zero past the 210 s mark. The pressures may also have different values depending on various factors, such as the volume of the chambers.

Figure 4:
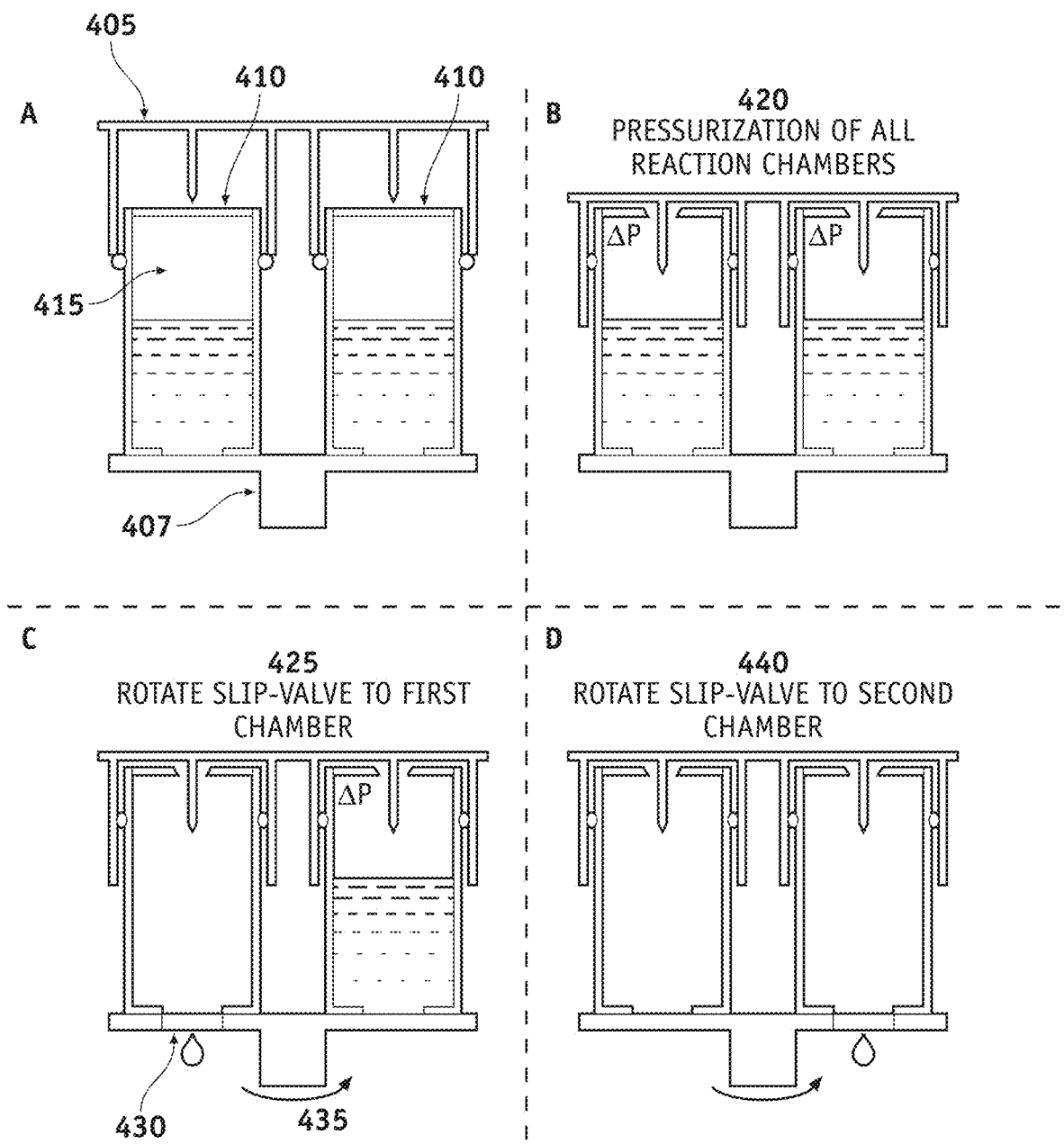
FIG. 4 illustrates an exemplary operation of a device.

The chambers within the device are compartments containing liquid reagents, such as, but not limited to, the liquid sample, wash buffers, elution buffers, internal control solutions, and negative control solutions. The reagents can be stored in compartments that are sealed with foils to prevent reagent evaporation. The use of pierceable blister foils for reagent storage and on-demand release can be combined with a rotational layer that contains a solid-phase column for analyte-capture, as illustrated in FIG. 4. That rotational layer can be referred to as a "Slip-Valve".

The Slip-Valve enables on-demand release of the liquid reagent from a reagent chamber when the solid-phase column from the rotational layer is positioned underneath said reagent chamber. One protocol that can benefit from such an automated process is the purification of nucleic acids from liquid samples. In a first step, a sample containing bacteria or viruses that are lysed to free their nucleic acids is pumped through a solid-phase column. For example, the sample can be put in a lysing buffer, and the lid of a device can be pressed down to pressurize a chamber, as described above in the present disclosure. The solid-phase column can be placed at the bottom of a chamber so that the liquid is forced to go through the column.

Subsequently, the column will rotate to the next reagent compartment, where a wash buffer is pumped through the solid phase column to remove impurities that were present in the sample. In other words, the solid phase column can be part of a rotating section which rotates (by manual or motorized activation) to connect different chambers. The solid phase column can be positioned underneath multiple reagent chambers that contain different wash buffers. Thus, different reagents can be pressurized by the lid activation, and by rotating the section containing the solid phase column, the column can be contacted to different chambers. The different reagents contained in the chambers can in turn be pushed through the column to replicate in a portable format the reactions commonly occurring in a laboratory setting.

In a further step, the solid phase column can be positioned underneath a reagent reservoir that contains an elution buffer to elute the purified nucleic acids. For example, the purified nucleic acids can be eluted in one or more chambers. In some embodiments, these purified nucleic acids can be analyzed, for example with nucleic acid amplification testing, sequencing, nucleic acid gels, or optically, and can be used in downstream processes such as nucleic acid amplification, cloning, ligation, cell-free transcription and translation.

FIG. 4 illustrates an exemplary design where foil-sealed reagent chambers are combined with a pumping lid technology, for storage and pressurization of these reagents. In panel a of FIG. 4, the reagent chamber (415) is sealed with foil (410) on top. The pumping lid (405) is ready to be pushed down. In some embodiments, the lysed sample is inserted into a chamber through an opening in the lid. In other embodiments, since the various chambers are sealed by foils, the lid can be removed to insert the lysed sample in the chamber, and subsequently the lid is inserted over the device, to be pressed down. In some embodiments, a separate device is used to lyse the sample. These lysing devices are known to the person of ordinary skill in the art, and may be portable. The output of these devices is, generally, a lysed sample in a lysing liquid buffer. The sample, in the liquid lysing buffer, can be inserted in a first chamber of the devices of the present disclosure.

In panel b, the pumping lid is placed on top of the reagent compartment and pushed down so as to create a seal (for example, with an O-ring situated on the outer concentric position) with the reagent compartments. Pushing the pumping lid down pressurizes the air on top of the liquid reagents, while breaking the foil with the piercer. In the example of FIG. 4, all chambers are pierced and pressurized simultaneously (420) by a single press of the lid. Underneath the reagent chambers there is a "Slip-Valve", a section of the device which can rotates relative to the upper part of the device, that is relative to the upper chambers. The Slip-Valve (407) seals off the reagent chambers and contains the solid-phase column (430) for capturing target analytes. The Slip-Valve can rotate and align the solid-phase column underneath a particular reagent chamber. For example, panel c shows the column (430) underneath a first chamber, while panel d shows the column after rotation, now underneath a second chamber.

When the solid-phase column (430) is aligned with a reagent chamber, the pressurized air in that chamber can pump the reagent of said reservoir through the solid-phase column, as illustrated in panels c and d. In other words, the pressurized chambers are sealed on the top by the lid, and on the bottom by the rotating section (the Slip-Valve). When the solid phase column is rotated underneath a pressurized chamber, the pressure forces the liquid or gas within it to escape through the column, thus continuing the sequence of reactions within the column.

In panel c, the rotating section rotates (425) the column (430) underneath the next chamber in the sequence (435). Further rotations (440) continue until the reactions are completed. After pumping a reagent from one reservoir through the solid-phase column, the Slip-Valve can rotate the column again to the next reagent chamber, as is illustrated in panel d. The pressurized air in the following chamber can now cause the reagent in this reaction chamber to be pumped through the solid-phase column. Pumping lid technology can be combined with these foil-sealed compartments and can be used to obtain pressurization of the stored liquid in combination with breakage of the seal, as illustrated in FIG. 4.

In some embodiments, the devices of the present disclosure can comprise a sample preparation module, and an amplification module. The sample preparation module will be described first, in the following. The sample preparation module and the amplification module can be used independently of one another, or in combination. The structure of the modules can be configured to be compatible, for example having slots and tabs that allow the two modules to attach to each other and rotate relative to each other.

The sample preparation module assembly can be realized in different ways. In the examples described in the present disclosure, the geometry of the sample preparation module was designed in CAD and printed using a multi-material 3D printer. The sample preparation module can comprise, in some embodiments, several different parts as in the following: (i) a pumping lid, e.g. (105) in FIG. 1; (ii) blister piercers, e.g. (107) in FIG. 1; (iii) a top section, or reagent section, e.g. (510) in FIG. 5; (iv) a top section, e.g. (535) in FIG. 5, which may support all the top chambers (540) and seal the chambers of the reagent section, e.g. (540), with the rotating layer (515); (v) a rotating layer, e.g. (515); (vi) a bottom or base layer, e.g. (520), which can contain other reaction chambers, and waste chambers to contain waste liquids from reactions occurring in the top reagent chambers; (vii) a bottom layer section, e.g. (550), including a plate to support the bottom chambers and seal the base layer with the rotating layer; (viii) a locking ring (555) which generates a compression force for sealing the other sections, forming a seal between the rotating layer with the top section plate and the rotating layer with the bottom section plate.

The different sections can be rotated in sequence according to the specified procedure, and they can be locked in each position of the sequence. The locking ring can be unlocked to rotate the sections to the next configuration.

Figure 5:
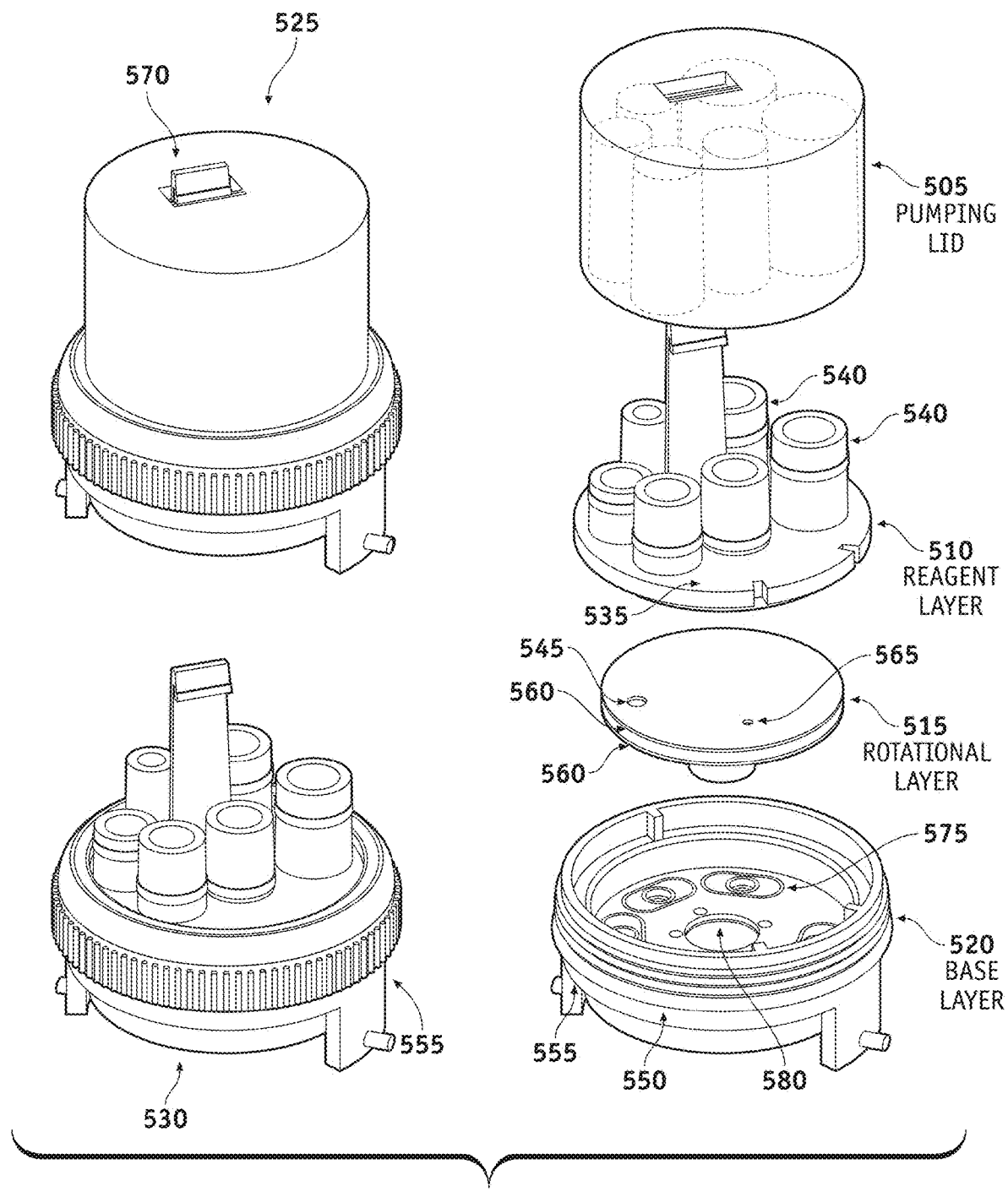
Figure 22:
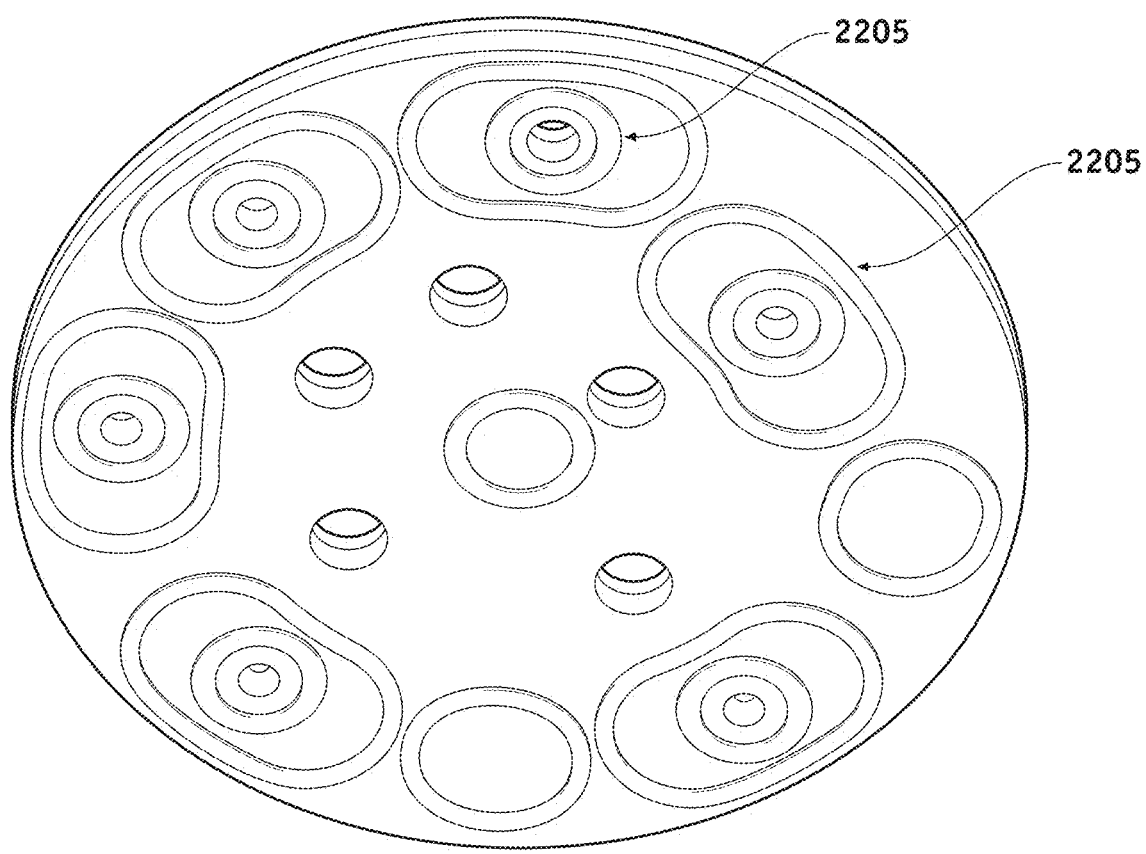
FIG. 22 illustrates the bottom surface of the plate sealing the top reagents to the rotating layer.

FIG. 5 illustrates an exploded view of an exemplary sample preparation module, comprising a pumping lid and different sections. Seals can be inserted between sections, for example using rubber O-rings, to maintain separation between sections and chambers. Several storage or waste chambers (575) are illustrated. The top of section (550) is a plate that seals against the rotating layer, while the bottom of section (535) is also a plate which seals against the rotating layer. The bottom plate of section (535) is illustrated in FIG. 22. FIG. 22 illustrates how the plate has ridges (2205) around each bottom opening of the reagent chambers in the top section. These ridges provide a seal between the rotating section and the top section with the reagent chambers. In some embodiments, as visible in FIG. 22, the ridges form two consecutive seals around several bottom openings for the chambers.

In some embodiments, the sample preparation module can be fabricated as in the following. The blister piercers are affixed to the pumping lid, and the inner cylinders of the pumping lid are greased with high vacuum grease. An appropriate lubricant, such as Krytox™ GPL 205 by DuPont™ is added to the bottom of the top layer plate, which is then affixed to the top layer. The same procedure is repeated for the bottom layer plate with the bottom layer. For the rotating layer, silicone rubber adhesive back sheets are punched in different diameters as needed for the specific device, e.g. using 42 mm, 4 mm, 1.5 mm, and 3 mm punches. These punches are to generate inlets and outlets. The adhesive rubber sheets are laminated onto the top and bottom faces of the rotating layer. Two silica membranes, for example 4.4 mm thick, are layered into the column of the rotating layer, and pressed into place with the cut tip of a male luer insert. A thin layer of lubricant was added to the top and bottom of the silicone sheets. For the bottom layer, one silica membrane was placed into the outlet for the negative control, in order to reduce the flow rate.

The rotating layer is first placed on top of the bottom layer, and the top layer is placed on top of the rotating layer. The rotating layer can rotate relative to the top section and to the bottom section, and allows moving the solid phase column (545,430) underneath different reagent chambers (540). The rotating layer may also have another opening (565), for example a waste opening. The bottom part may contain chambers (575) for waste storage. For example, there may be one waste chamber for each top chamber that generates waste. For example, if a reagent is flown through the solid phase column from a top chamber, the waste liquid may flow through the column into a corresponding bottom chamber which is connected through a fluidic channel formed by aligning the rotating layer accordingly, so that the column forms a connection between the top chamber and the bottom chamber. When the nucleic acids are eluted from the column, they flow with the liquid into a bottom chamber (575), for storage or alternatively through a channel for collection or to a second module. Therefore, the bottom chambers can be used for storage of waste or of samples. FIG. 5 also illustrates an opening (580) which can be used to insert a motor shaft if the rotation is to be applied with a motor.

Figure 6:
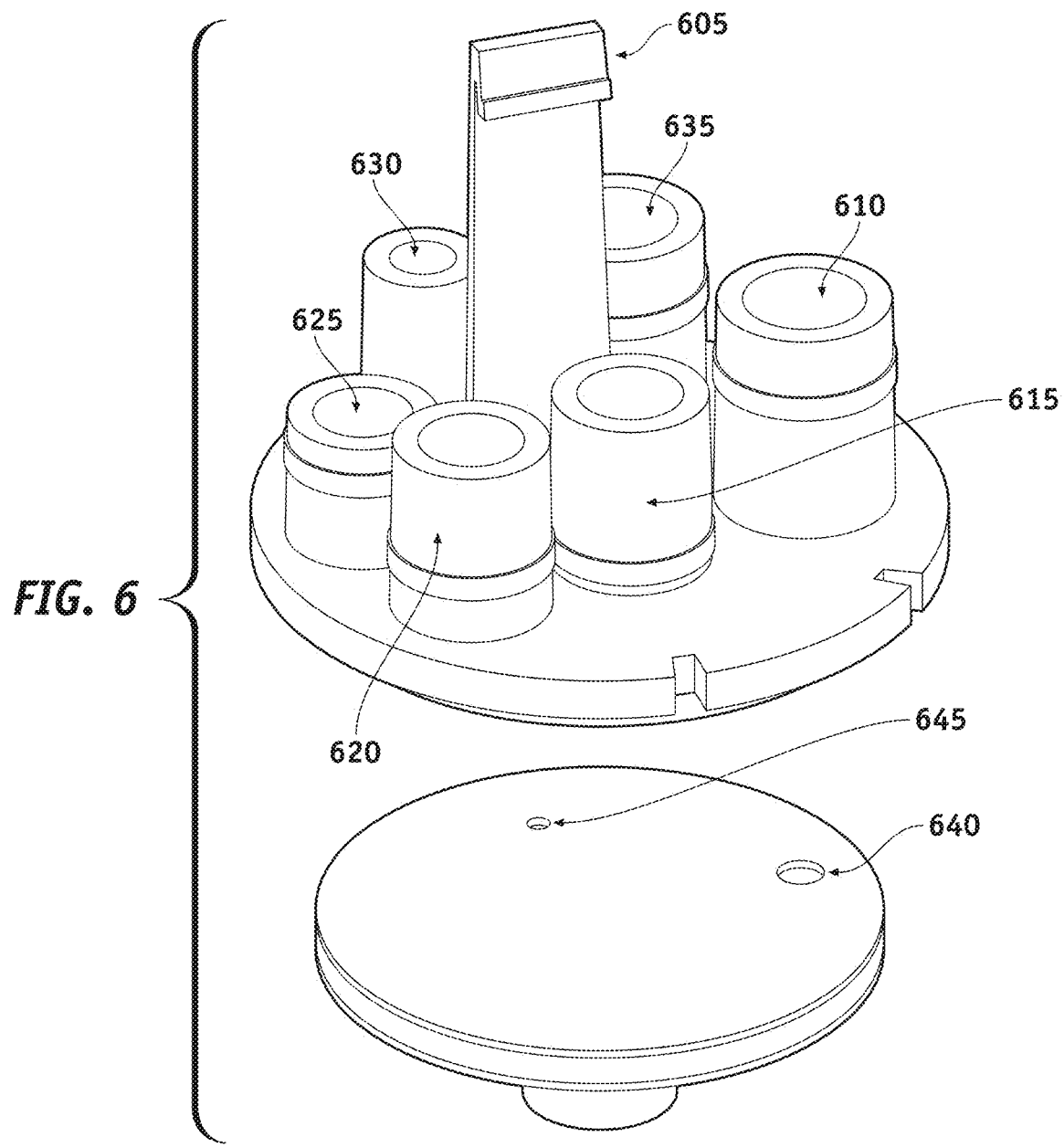

FIG. 6 illustrates some parts of an exemplary sample preparation module in more details. The tab (605) is configured to insert into the pumping lid, as can be seen in FIG. 5 (570). In some embodiments, the sample preparation module may comprise a chamber (610) where the sample containing the biomolecules of interest is inserted. For example, the pre-lysed sample may be inserted with a lysis buffer in (610). Chamber (615) may contain water for a negative control. Chamber (620) may contain water for the main reactions. Chamber (625) may optionally contain air to dry the sample during processing. Chambers (630,635) may contain wash buffers, for example for octanol. Chambers may be sealed with foils as described in the present disclosure. The rotating layer underneath may have one or more openings (645) to form fluidics channels by connecting the top chambers to the bottom chambers in other parts of the device. A solid phase column (640) is used during the sample processing, and also forms fluidic channels by connecting underneath different top chambers and bottom chambers. The tab can be any locking mechanism which holds the pumping lid in place after pressurization. The tab prevents the user from opening the device, minimizing exposure to potentially infectious materials and chemical reagents.

When assembling the module, the locking ring is rotated onto the assembly, which compresses the rotating layer between the top and bottom layers, generating liquid-tight seals. In some embodiments, the following reagents and liquids can be used for the various reaction chambers. For example, 700 µL of Viral DNA/RNA wash buffer (by Zymo™) was added to the (first) wash chamber; 300 µL octanol was added to the octanol chamber (i.e. the second wash chamber); 300 µL nuclease-free water (NF-H2O) was added to the eluent chamber; and 300 µL NF-H2O was added to the negative control chamber. A 4 mil Mylar™ foil was laminated with a double-sided adhesive and punched into 10 and 15 mm diameter circles. The Mylar™ foil was attached to the top of each chamber containing liquid to form sealing foils.

Therefore, in some embodiments, the sample preparation module may comprise a first chamber to contain a lysed sample (e.g. 1 volume patient urine+1 volume 2×DNA/RNA Shield by Zymo™, and 4 volumes Viral DNA/RNA buffer by Zymo™); a second chamber with a Viral wash buffer by Zymo™; a third chamber with 1-octanol; a fourth chamber with air; a fifth chamber with an elution liquid (e.g. NF-H2O); and a sixth chamber for a negative control (NF-H2O). In other embodiments, different reagents may be used.

The following description describes an exemplary device for purification of analytes from a sample, such as blood, urine, plasma or serum samples. The device contains multiple reagent chambers that contain reagents needed for purifying analytes, such as nucleic acids or proteins from the sample. The device consists of three layers, of which the base layer and the reagent layer are stationary, with a mobile rotational layer in the middle. The rotational layer contains a solid phase material for the purification of analytes, such as silica, also referred to as a column. A fluidic seal is obtained between both sides of the rotational layer and the base layer and the reagent layer. Fluid is only allowed to pump through the solid phase column of the rotational column when said rotational column is positioned underneath a reagent reservoir.

The liquid present in the reservoirs is pressurized by the pumping lid that compresses the air on top of the liquid reagent after breaking the foils on top of the liquid reagent compartments. The pumping lid pressurizes all liquid reagents upon actuation, but the pressure generated is only released when the solid phase column present in the rotational layer is positioned directly underneath the outlet of a liquid reagent reservoir in the reagent layer.

When a liquid is pumped through the solid phase column of the rotational layer, it is captured in a waste compartment present in the base layer of the device if the reagent is to be discarded. Alternatively, the liquid can be pumped through to a subsequent device component, which would be the case for eluded target analytes such as nucleic acids. The target analytes, e.g. the nucleic acids, are then sent to a device component where amplification of said nucleic acids will be carried out. One or more concentric holes in the rotational layer can be utilized for the pumping of multiple solutions to different chambers or the same chamber, such as a negative control solution. Pressure can be pre-programmed during the device design, for example by altering the height of the pumping lid, the height of the seal, the height of the chamber, the diameter of the chamber, and the volume of the sample. Since all these factors affect the pressure, and they can be controlled during the device fabrication, the desired pressure for each chamber can be controlled accordingly.

FIGS. 7-8 illustrates a multi-chamber design of a sample preparation module, which includes a pumping lid (705), a reagent layer (710), a rotating layer (715) with a solid-phase column, and a base layer (720). To exemplify the device's operation, the device is shown in two different positions in FIGS. 7-8, in between which the rotating layer rotates the solid phase column from one reagent chamber to another. The rotational position of the rotating layer is the only device component that moves, while the other device components remain stationary. FIG. 7 illustrates an outer view of the module (730), as well as a cross section view (725). The cross section illustrates reagent chambers such as (735); a solid phase column (755) aligned with chamber (735); a bottom chamber (760) into which the liquid from chamber (735) is input after flowing through the column; other bottom chambers and fluidic pathways (740); and a central shaft (750) for optional connection to a motor, or to enable the device rotation.

Figure 9:
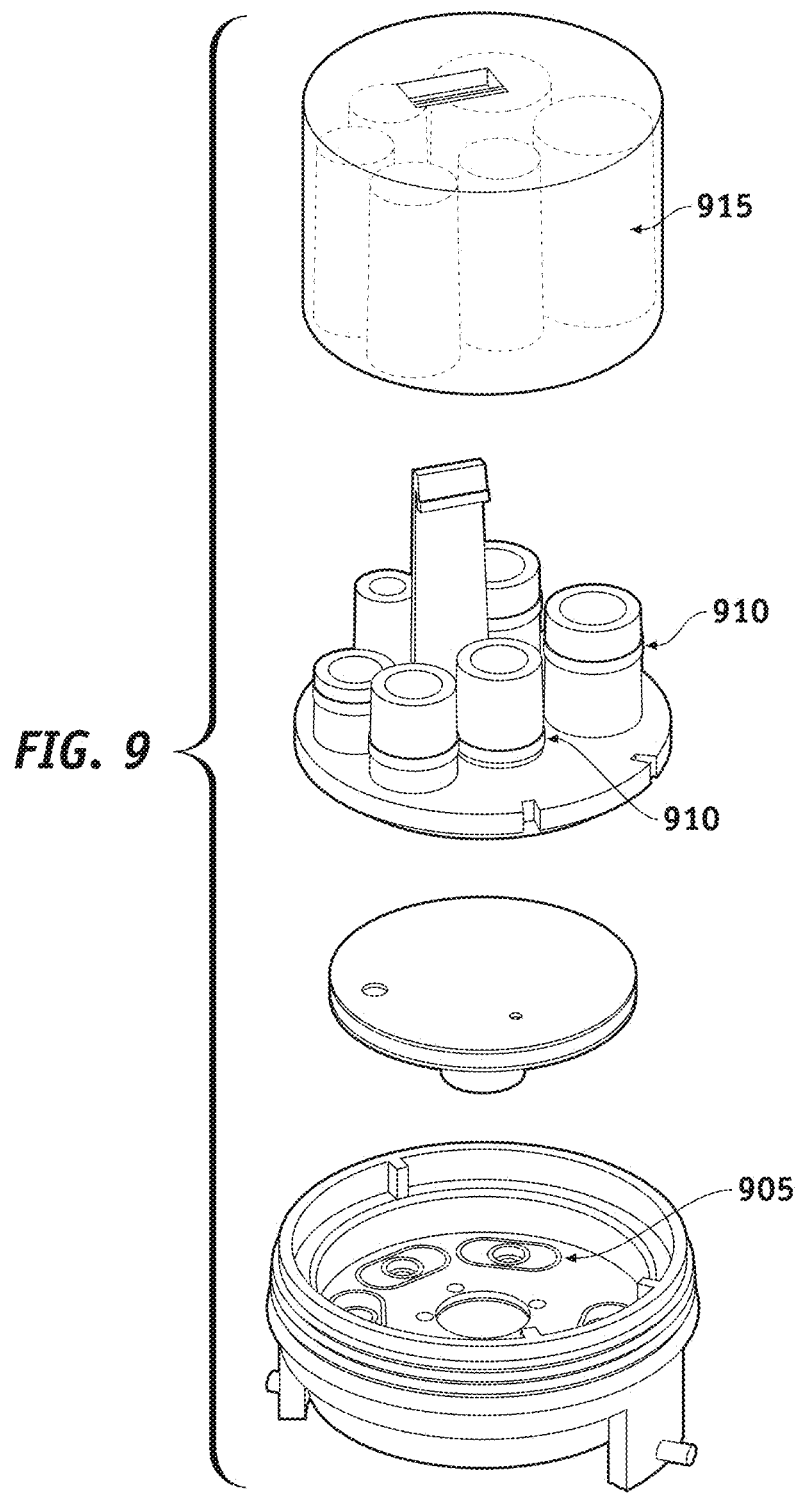
Figure 10:
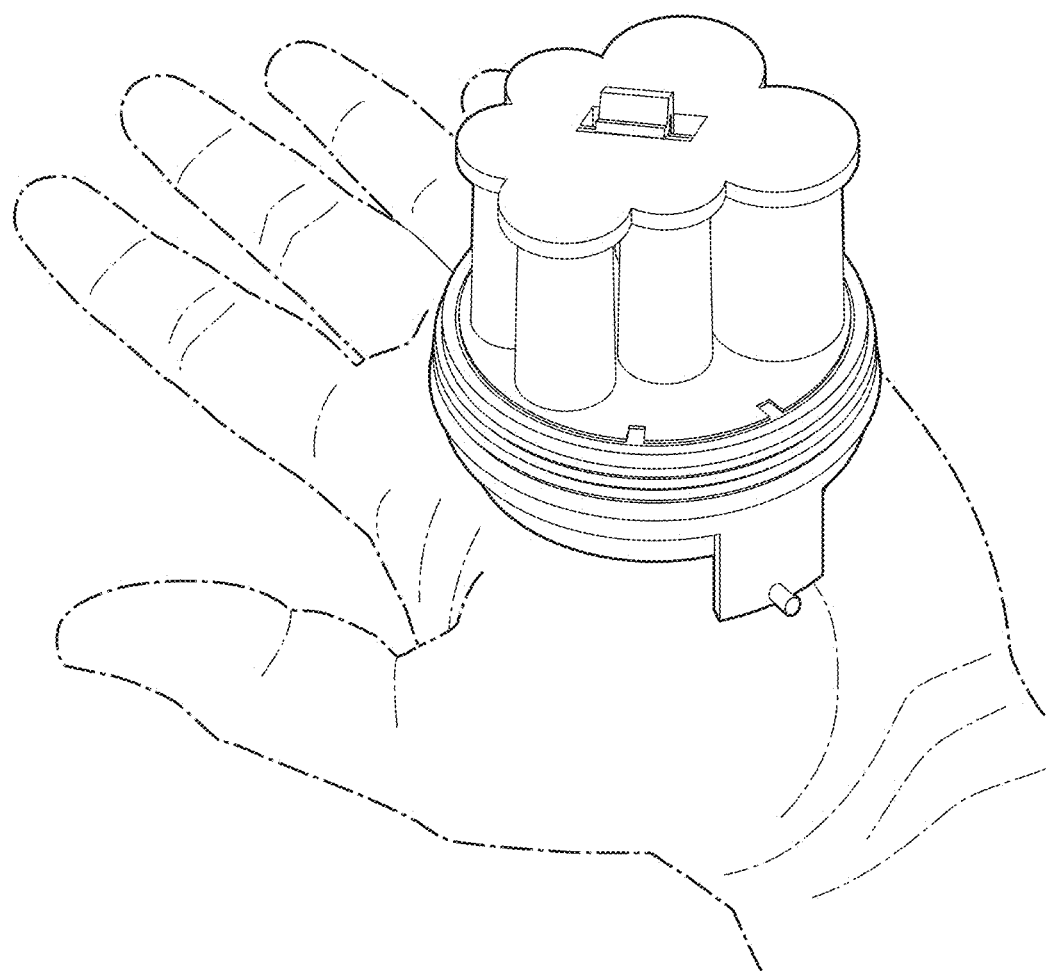
Figure 11:
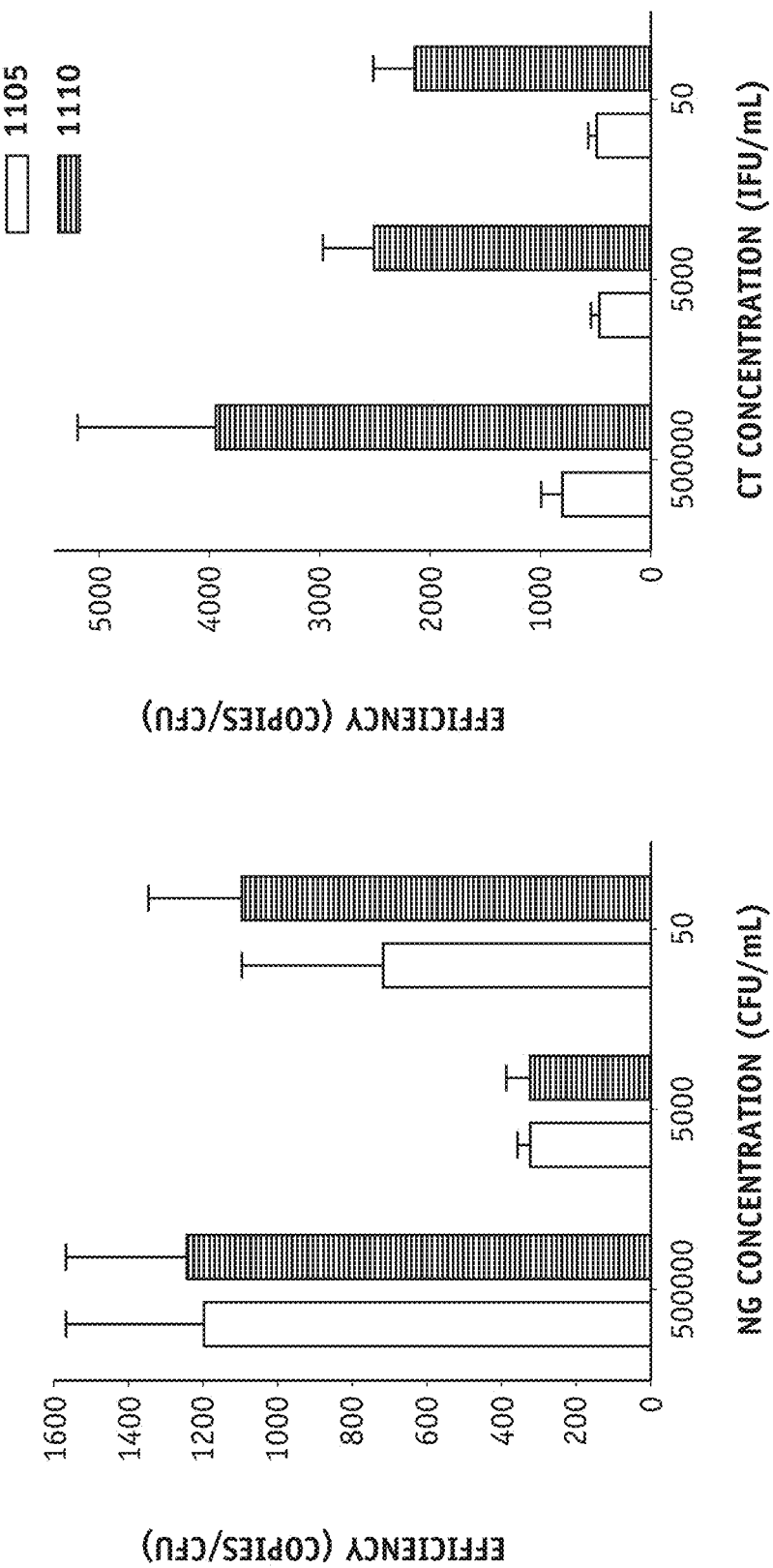
FIG. 11 illustrates exemplary data.

FIG. 8 illustrates the module of FIG. 7, with a rotated position. The column (805) is now in a different position compared to that of FIG. 7. The column (810) is therefore aligned with a different chamber compared to FIG. 7. FIG. 9 illustrates an exploded view of the sample preparation module, illustrating different bottom chambers (905). Seals (910) are placed around the reagent chambers, to form a seal with the corresponding cylinders (915) in the pumping lid. FIG. 10 illustrates a relative size comparison of an exemplary sample preparation module with a human hand. FIG. 11 illustrates comparative data for a device as described in the present disclosure, compared to a standard, non portable, laboratory protocol.

FIG. 11 illustrates the performance of a multichamber sample preparation device that sequentially pumps a lysed sample, wash buffers and elution buffer through a solid-phase column. The performance of the device is compared to a known standard method, a Qiagen™ RNeasy™ kit. The samples that were analyzed were urine samples that were spiked with a certain concentration of bacteria, *Chlamydia Trachomatis* (CT) and *Neisseria Gonorrhoeae* (NG). Concentrations of NG are reported as colony-forming units per milliliter (CFU/mL) and concentrations of CT are reported as inclusion-forming units per milliliter (IFU/mL). Spiked urine samples were mixed with lysis buffer, and were added to the multichamber device. After placing the pumping lid on the device, the lysed sample, wash buffers and elution buffer were sequentially pumped through a solid-phase silica purification column. The resulting eluates were collected in polymerase chain reaction (PCR) tubes and were analyzed by digital reverse transcriptase polymerase chain reaction (dRT-PCR). The resulting number of ribonucleic acid (RNA) copies per bacterial cell (reported as copies/CFU) was compared to the standard method, i.e. a Qiagen™

RNEasy™ kit. As can be seen from FIG. 11, the device of the present disclosure (1110) extracted at least as much RNA/CFU as the standard laboratory kit (1105).

As described above in the present disclosure, a multi-chamber sample preparation module comprises a pumping lid used for pressurization of reagents that are contained within the reagent layer. The reagent layer is composed of multiple reagent reservoirs that can contain liquid reagents, and includes an elastomeric seal on the outer diameter of said reservoirs. The cylinders present in the pumping lid fit over the reagent reservoirs of the reagent layer, and when the inner cylinder walls of the pumping lid seal with the outer walls of the cylinders of the reagent layer, pressure is generated in every reagent compartment. The rotating layer contains a column for capturing analytes from a sample, and can contain other openings, such as for example an opening for pumping a negative control sample. In some embodiments, the reagent layer and base layer will be stationary after assembly, whereas the rotating layer can rotate and place the column underneath every reagent reservoir in the reagent layer in a sequential fashion.

In the following, an amplification module is described. In some embodiments, an amplification module can be fabricated using a combination of laser cutting and multi-material 3D printing. An exemplary amplification module can comprise 4 primary components: (i) a top plate, (ii) a bottom plate, (iii) inner and outer pins, and (iv) inner and outer clamps. A layer of adhesive tape was laminated on the top sides of both top and bottom plates. The top (e.g. 2.1 mm thick) and bottom plates (e.g. 1.5 mm thick) were laser cut from cast acrylic, using vector cutting to generate the outline, wells, and outlets, and using engraving for the channels. A laser-cut donut of 0.175 mm poly(methyl methacrylate) (PMMA) was solvent bonded onto the bottom of the bottom plate using 20% dichloroethane in ethanol, to form the bottom of the wells. The laser-cut donut may also be attached with an adhesive. The thin-film PMMA was held against the bottom plate by sandwiching between 3 glass slides on both sides, and holding the assembly together with binder clips overnight. A thin coat of Krytox™ GPL 205 was applied by smearing it between two glass slides and stamping the top of the bottom plate. The wells were rinsed with 30 µL NF-H2O. The appropriate loop mediated isothermal amplification (LAMP) mix was added to each respective well, and bottom plates were lyophilized overnight. The bottom side of the top plate was stamped with Krytox™ GPL 205. Discs of polypropylene hydrophobic membranes (0.22 micro), 3 mm thick, were applied, covering the outlets of the top plate.

Following lyophilization, the bottom plates were removed from the lyophilizer under dry nitrogen and placed into a dry nitrogen glove bag. Bottom and top plates were sandwiched together, and clamps using inner and outer pin and clamp sets. The assembled amplification modules were stored in their slipped position, vacuum sealed under dry nitrogen in Mylar™ bags (4 mil), and stored at −20° C.

In some embodiments, the amplification module can be used for the amplification of nucleic acid molecules of a target nucleic acid from an infectious disease agent, such as bacteria or viruses. The amplification module comprises two plates, which can be moved rotationally or linearly relative to each other, to connect or disconnect wells and channels. FIGS. 12-15 illustrate an exemplary operation of the amplification module.

Figure 12:
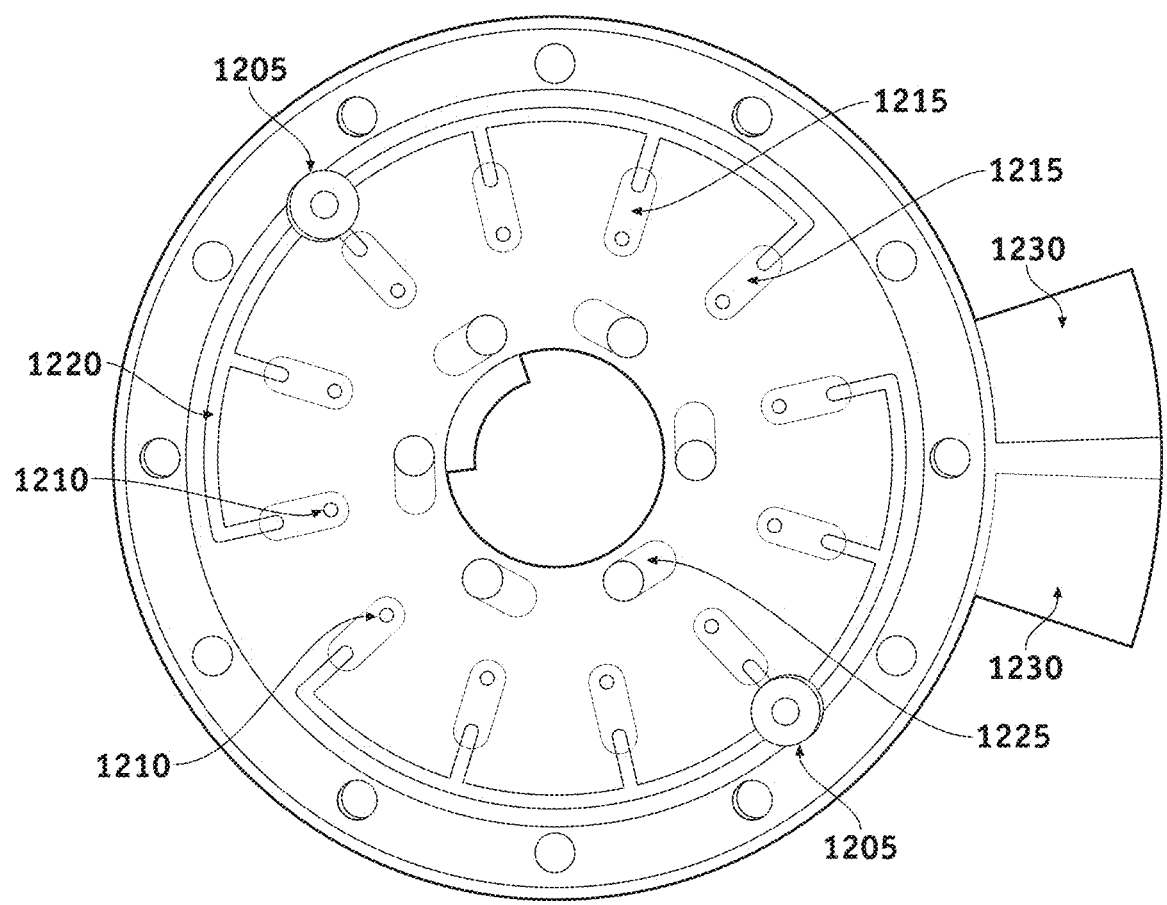
FIGS. 12-15 illustrate the operation of an amplification module.
Figure 13:
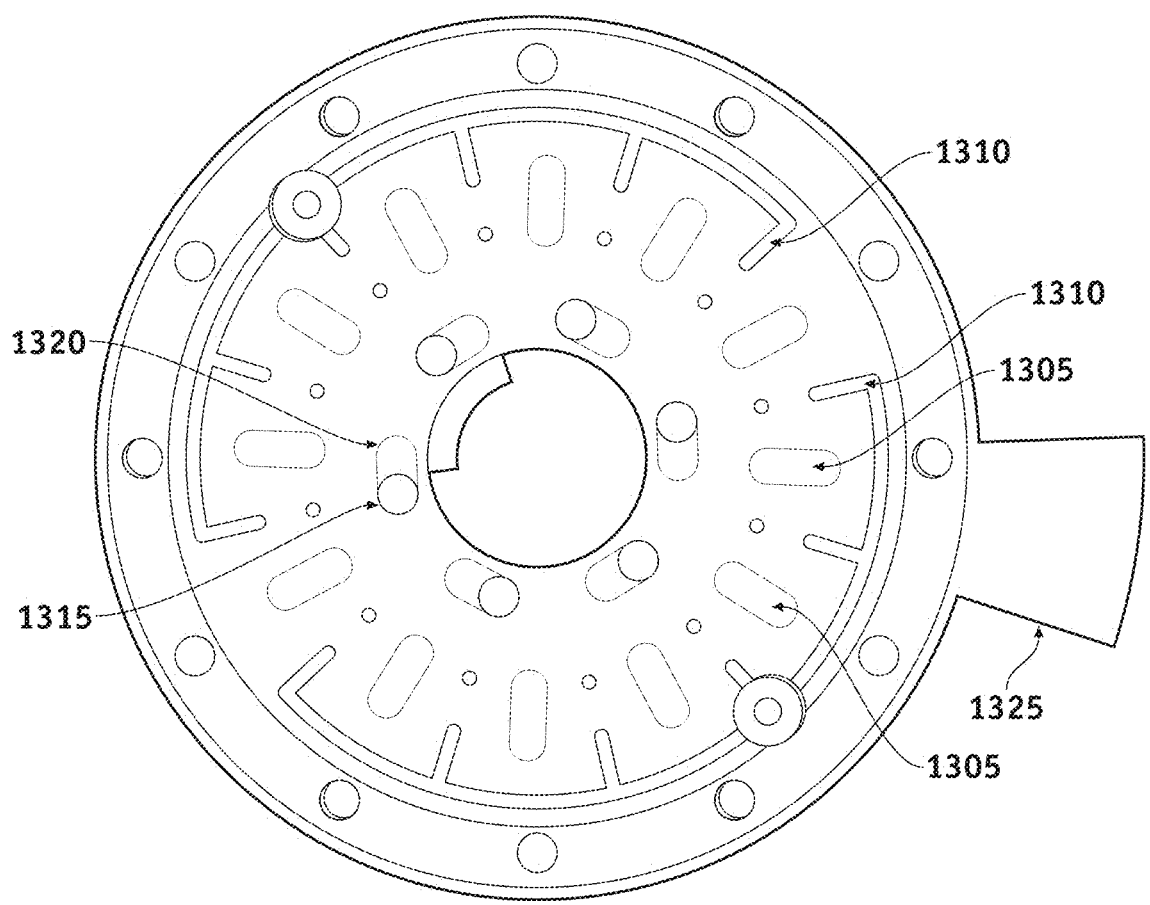

An amplification device comprises two plates that can be moved relative to one another. The exemplary device has two inlets (1205) for inserting liquids, and outlets (1210) for each reaction well (1215). In other embodiments, different number of inlets or outlets may be used. In this example, each reaction well (1215) has a corresponding outlet (1210), and is connected to one inlet (1205) through a fluidic channel (1220). In this example, each of the two inlets has its own separate channel that connects to the respective set of reaction wells. Liquid flowing into the device fills all the reaction wells in parallel. Upon slipping (rotating) of the bottom device layer, the reaction wells are disconnected from each other. FIG. 12 illustrates a first position where the reaction wells are connected to the inlets through the fluidic channels. FIG. 13 illustrates a second position where one plate is rotated relative to the other, disconnecting the reaction wells (1305) from the fluidic channels (1310). It can be understood that one plate holds the reaction well, while another plate holds the inlets and fluidic channels. FIG. 12 also illustrates tabs (1225) in a first position, while FIG. 13 has tabs in a second position (1315). In some embodiments, these tabs can be used to stop against corresponding slots (1320), defining the two positions. In this way, the rotation of one plate relative to the other can be carried out precisely. The slots can be located in one plate while the corresponding tabs can be located in the other plate. FIG. 12 illustrates how the external tabs which enable the manual rotation of the device (1230) are misaligned, while tabs (1325) are aligned; each tab is attached to a different plate.

The amplification module allows different reagents to be dried down or lyophilized into every reaction well, enabling multiplexing. The eluted nucleic acids, for example, or other target analytes, can be inserted in parallel in each reaction well, enabling the parallel analysis of the same sample, with different reagents. The same sample can therefore be tested, for example, for different diseases at the same time. Reagents that are to be lyophilized, such as enzymes, buffer salts, nucleic acid molecules (primers) and surfactants can be pipetted or dispensed in every reaction well. The plate in which these reagents are dispensed can subsequently be lyophilized or air-dried for drying down the reagents. Subsequently, the other plate of the device can be placed on top for assembly. Each amplification module can therefore be prepared in advance for specific purposes.

Figure 14:
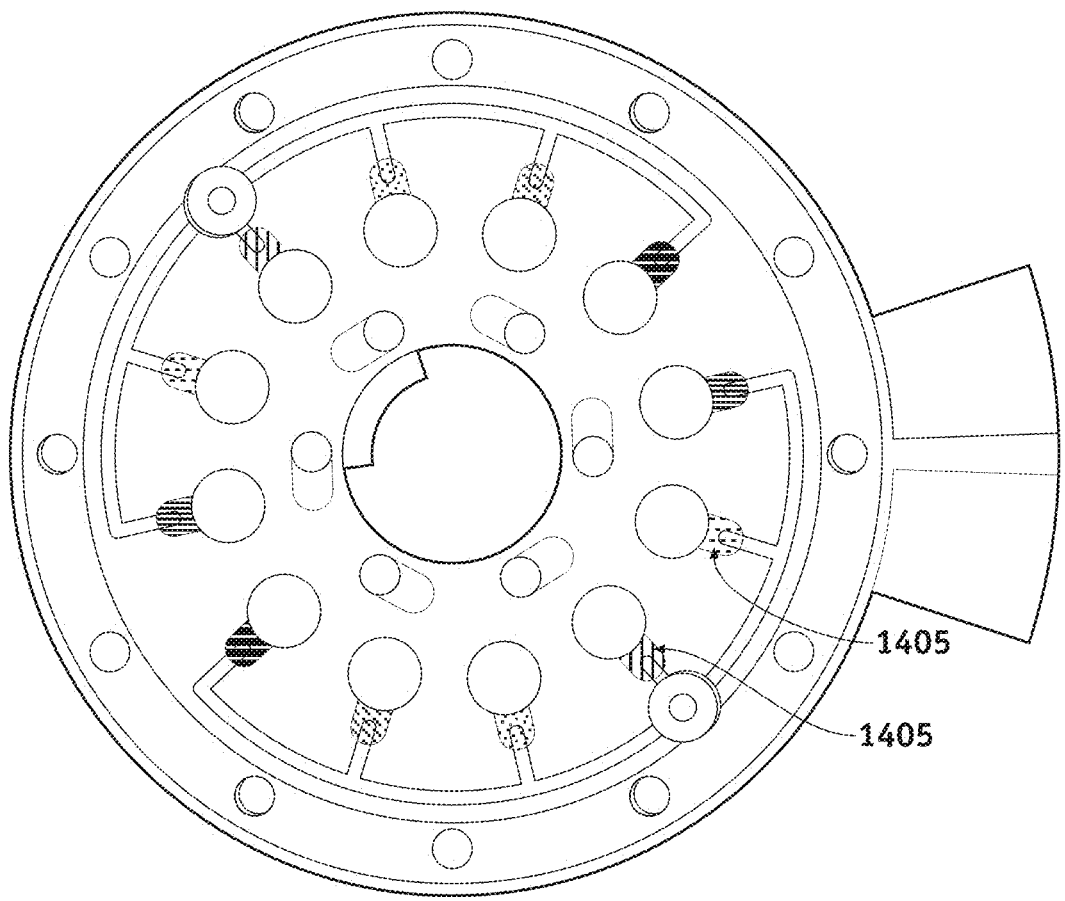
Figure 15:
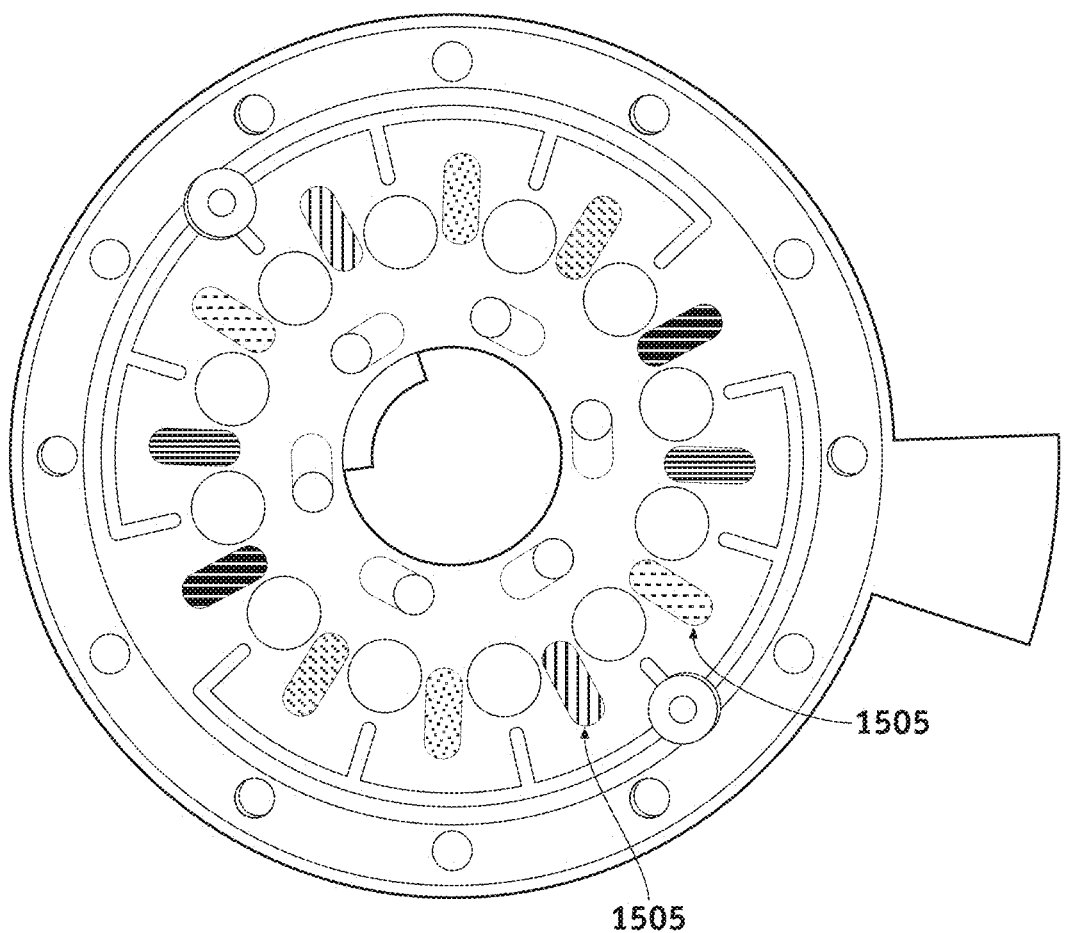

The filling of the reaction wells with the target analyte (from the inlet to the outlets) can happen in a serial or parallel fashion. FIGS. 14-15 illustrate an example for parallel filling of a device. Multiple dyed reagents (1405) were lyophilized inside the bottom plate of a device, followed by assembly. Each of the reaction wells can be prepared with a different reagent. In this example, a total of 12 wells is shown, with 6 wells connected to one inlet and 6 wells connected to another inlet. In this example, six wells were filled with water by dispensing it into one inlet, thus rehydrating the reagents. The other six wells were addressed by the other inlet. Hydrophobic membranes were placed on the outlet of every well, ensuring that air can escape while liquid cannot pass any further. The hydrophobic membranes allow air flow while blocking water flow, and greatly facilitate the filling of the reaction wells, which may otherwise not be possible. This procedure also serves as a metering mechanism. Upon slipping (rotating of one plate relative to the other), the different wells are now compartmentalized, as illustrated in FIG. 15, with no observable cross-contamination between the different wells.

Figure 16:
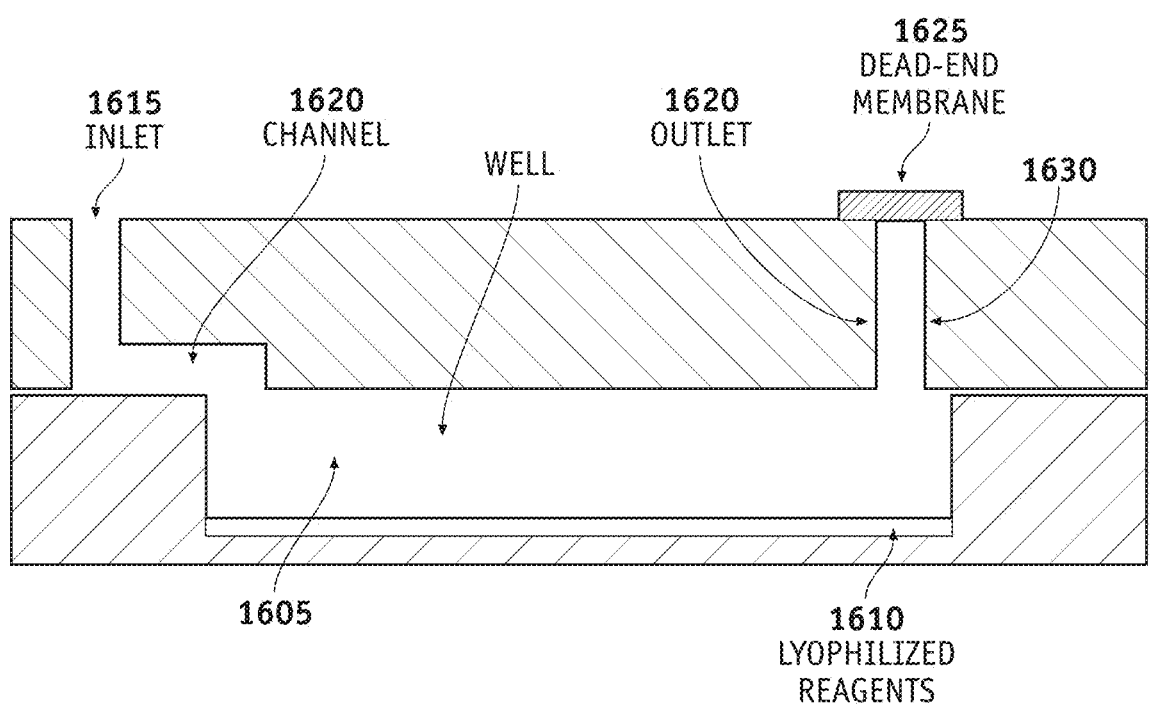
FIG. 16 illustrates a chamber with lyophilized reagents.

FIG. 16 illustrates an exemplary cross view of a reaction well (1605), with a bottom layer of lyophilized reagents (1610). A liquid can be inserted from the inlet (1615), through the fluidic channels (1620). FIG. 16 also illustrates an outlet (1625) for the reaction well, and a dead-end membrane (1625), permeable to air but impermeable to water. In some embodiments, a small dead end space (1630) can be left, and is meant to be filled with liquid. For example, this dead end volume can be about 10% of the volume of the well, in order to be small enough to not affect the concentration of the reagent once rehydrated. The dead volume facilitates filling of the well with liquids.

The device of FIGS. 15-16 was produced by laser cutting of acrylic (PMMA) sheets that were laminated with a double-sided acrylic adhesive elastomeric layer (also acrylic) of 170 um thickness. A lubricant was applied between both plates to assist sealing and lubrication for movement of one plate relative to the other.

Figure 17:
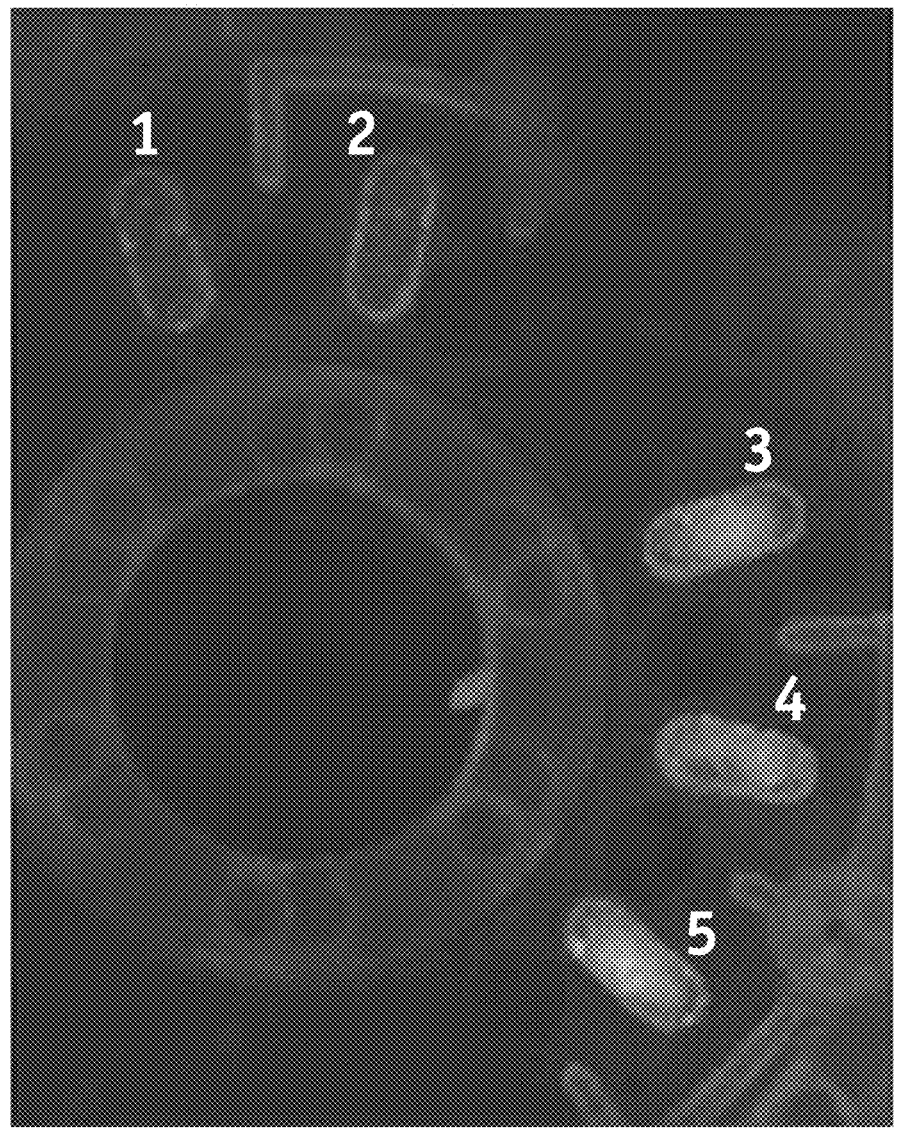
FIG. 17 illustrates a fluorescence image of an amplification module used for the detection of a disease.

FIG. 17 illustrates a fluorescence image from an amplification module in which target nucleic acids from *Neisseria Gonorrhoeae* were amplified within the module with lyophilized reagents in the reaction wells. Wells 1 and 2, illustrated in FIG. 17, were wells in which a negative control sample was introduced. Wells 3, 4 and 5 received target nucleic acids from a 5000× dilution from an eluate that contained purified nucleic acids from a urine sample, spiked with 5000 colony-forming units per milliliter of urine (CFU/mL) of *Neisseria Gonorrhoeae*. Hence, the introduced eluate corresponded to an equivalent amount of 1 CFU/mL.

Figure 18:
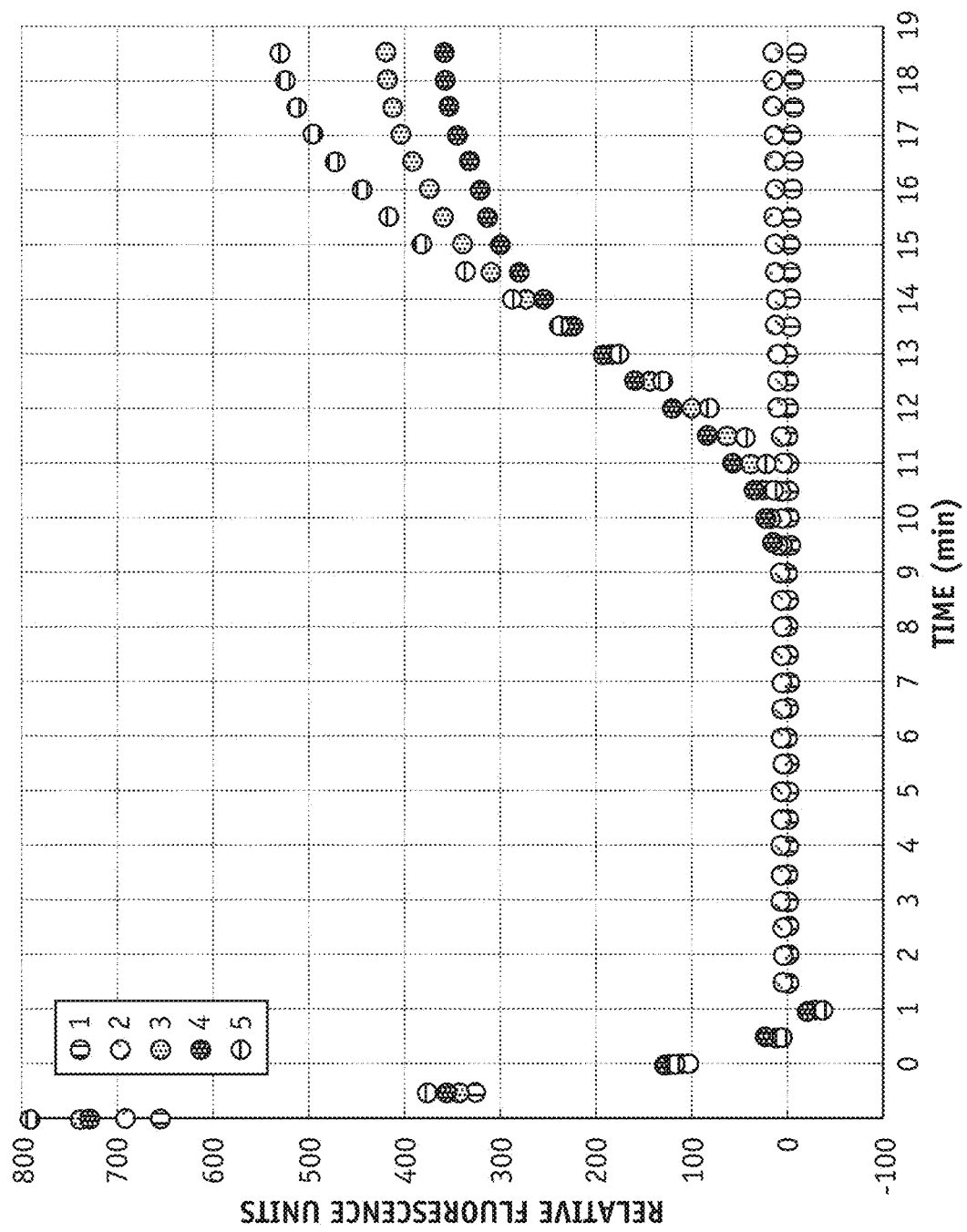
FIG. 18 illustrates data for the image of FIG. 17.

FIG. 18 illustrates the real-time fluorescence, data after baseline correction, corresponding to FIG. 17, showing that amplification with the lyophilized reagents starts as soon as 12 min after the start of the amplification procedure. The fluorescence image of FIG. 17 shows what the exemplary device looks like after 20 min of amplification, resulting in a distinguishable difference between the target nucleic acids and the negative control.

Figure 20:
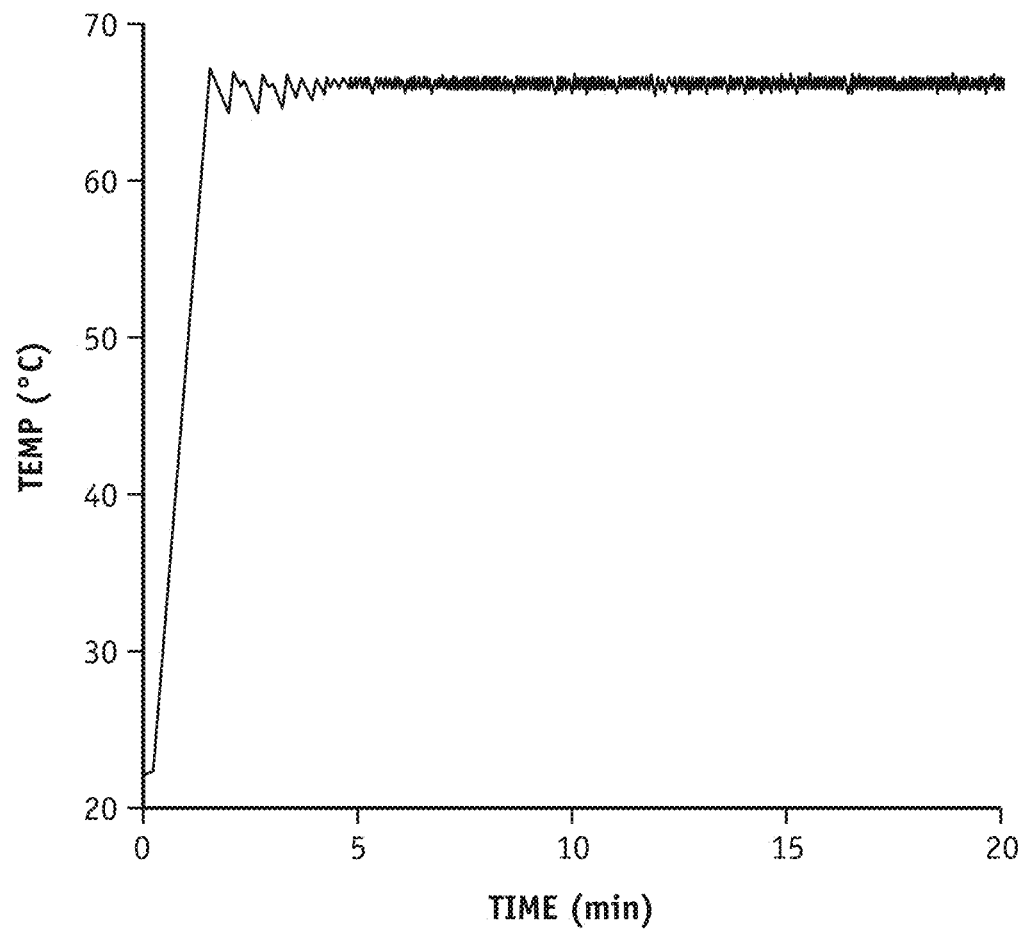
FIG. 20 illustrates an exemplary temperature profile when heating is activated in a device.

As known to the person of ordinary skill in the art, the reactions carried out in the devices of the present disclosure may require, or benefit, from temperature control. A heater can therefore be included in the devices described herein. A motor may also optionally be included. For example, a microstepping motor may be used. Other components may comprise gears or a gear-train, and a thin film heater. Electronic circuits can be included in the device or base station to control the heater and motor. A geared spring may also be incorporated in the rotation mechanism. A Geneva mechanism may be used for timing control. For example, heating for standard LAMP temperatures can be in the range 60-73° C.; isothermal amplification temperatures can be between 20 and 80° C.; standard PCR with thermocycling can have temperatures in the range between 45° C. to 98° C. FIG. 20 illustrates an exemplary temperature profile when heating is activated. In some embodiments, the heater and motor are part of the base station to which the amplification module, or the whole device comprising the amplification module and the sample preparation module, can be attached.

FIG. 19 illustrates a multi-chamber design which can be inserted in a driving shaft and rotated by the rotary mechanism until a locking mechanism locks the rotating plates and sections in place. For example, a pin and pin guide mechanism can be used. Once locked the device is locked to the motor, the driving shaft drives the rotating layers of the multi-chamber design. Reverse operation of the driving shaft brings the multi-chamber design out of the enclosure, unlocking it for easy removal. Through rotation, slipping of the SlipChip or amplification module can be performed. Panel a shows the integrated devices before locking. The pin (1910) rotates within the pin guide (1907) in a bayonet coupling. There is no activity with the slip mechanism (1905) of the amplification module at this point, as the device is being locked onto the driving shaft. Panel b shows the integrated device in the locked position and during operation of the rotational layer. The pin has rotated into the guide and is now locked into place (1915). At this point, further motor rotation causes the rotational layer with the slip column to rotate within the device. Panel c shows reverse rotation for easy removal and automated slipping of the amplification device. With a reverse slip, the pin (1920) disengages from the guide and the amplification module slip feature (1930) collides with block (1925) to slip the amplification module. Panel c shows the tabs in the slipped position (1930), compared to the unslipped position (1905). The slip mechanism refers to the relative positions of the first and second plates, connecting or isolating the reaction wells from the microfluidic pathways, as illustrated in FIGS. 14-15.

In some embodiments, the sample preparation module and the amplification module can be connected to form a single multi-functional device. Fluidic channels allow passage from the top chambers of the sample preparation module, through the solid phase column, into the bottom chambers of the sample preparation module. The purified nucleic acids, or other target analytes, stored in the bottom chamber of the sample preparation device, can subsequently be inserted into the reaction wells of the amplification module. The storage chamber in the sample preparation module is connected to the inlets of the amplification module, allowing passage of the liquids between the modules upon activation. For example the amplification module is rotated to align the inlet with the storage chamber, allowing passage of the target analyte. In some embodiments, a single outlet of the storage chamber can connect to both inlets of the amplification module at the same time. In some embodiments, the storage chamber for the target analyte connects to one inlet of the amplification module, while the chamber of the negative control connects to the second inlet. Each of the wells of the amplification module can test for a different disease, for example.

In some embodiments, the amplification module processes the sample by heating, while being attached to the base station. Subsequently, the amplification module is removed from the base station and can be imaged with fluorescence. For example, the reaction wells of the amplification module may be transparent on the bottom. For example, the reaction wells may be covered by a thin acrylic film which is transparent. A device to carry out fluorescence imaging can then be attached to the bottom of the amplification module. For example, a smartphone with a light source and sensor (a fluorescence detector) may be used for this purpose, allowing fluorescence imaging to be carried out in the field instead of a laboratory setting.

In some embodiments, the wash buffers may be ethanol and octanol, or mixtures thereof. The elution buffer may be water. With regard to the nucleic acid extraction chemistry: The lysis buffer containing chaotropic salts such as guanidinium isothiocyanate lyses the bacteria in the sample thereby releases nucleic acids. The lysis buffer also deactivates nucleases. The nucleic acids bind to silica column. The wash buffer, typically containing ethanol between 50-100%, washes the silica column. For elution, typically nuclease-free water or tris-ethylenediaminetetraacetic acid (EDTA) (TE buffer) is used to rehydrate the purified nucleic acids from the column. In some embodiments, the piercers of the lid have a length extending from a top end to a bottom end of each chamber. In some embodiments, the wash buffer liquid can be 1-octanol, or an alcohol with a chain length greater than 5. In some embodiments, the rotating section, the first plate, and the second plate each comprise a central opening configured to accept a motor shaft for motorized rotation of the rotating section, the first plate, and the second plate. In some embodiments, the amplification module, the device comprising the sample preparation module and the amplification module, the base station, or an additional device, for example attached or, or part of, a smartphone, may comprise a fluorescence imager for measuring fluorescence of the reaction wells.

In some embodiments, instead of the lid having piercers which pierce through the foils or membranes sealing the reagents within the chambers, it is possible to use other methods for sealing and releasing the reagents, e.g. the wash buffers. For example, pressure membranes can be used, which burst upon a threshold pressure value. For example, a foil or pouch may be inserted in a reagent chamber. The pouch would entirely enclose the liquid reagent. Since the lid forms an air seal with the chambers, in order to pressurize the chambers, the increased pressure would be able to burst open the pouch. In some embodiments, one or more weaker points, or designed failure points, can be prepared in the pouch to cause it to burst at those preferred failure points. For example, the failure point may be a thinner patch in the pouch, which would preferentially break first. The pouch may be attached to the chamber forming an airtight connection with the chamber at specific points, in order to better control how the pouch bursts and releases its content. In other embodiments, instead of using membranes or pouches, it is possible to use pressure-activated valves. For example, a pressure activated valve can be inserted at the openings in the top of each chamber, and the bottom of each reagent chamber. The valve will remain close, sealing the chamber, until a pressure value is reached; the pressure value will open the valve, allowing the liquid to go through. In some embodiments, the reagent chambers can be loaded manually, for example with a pipette, without using foils or membranes.

Figure 21:
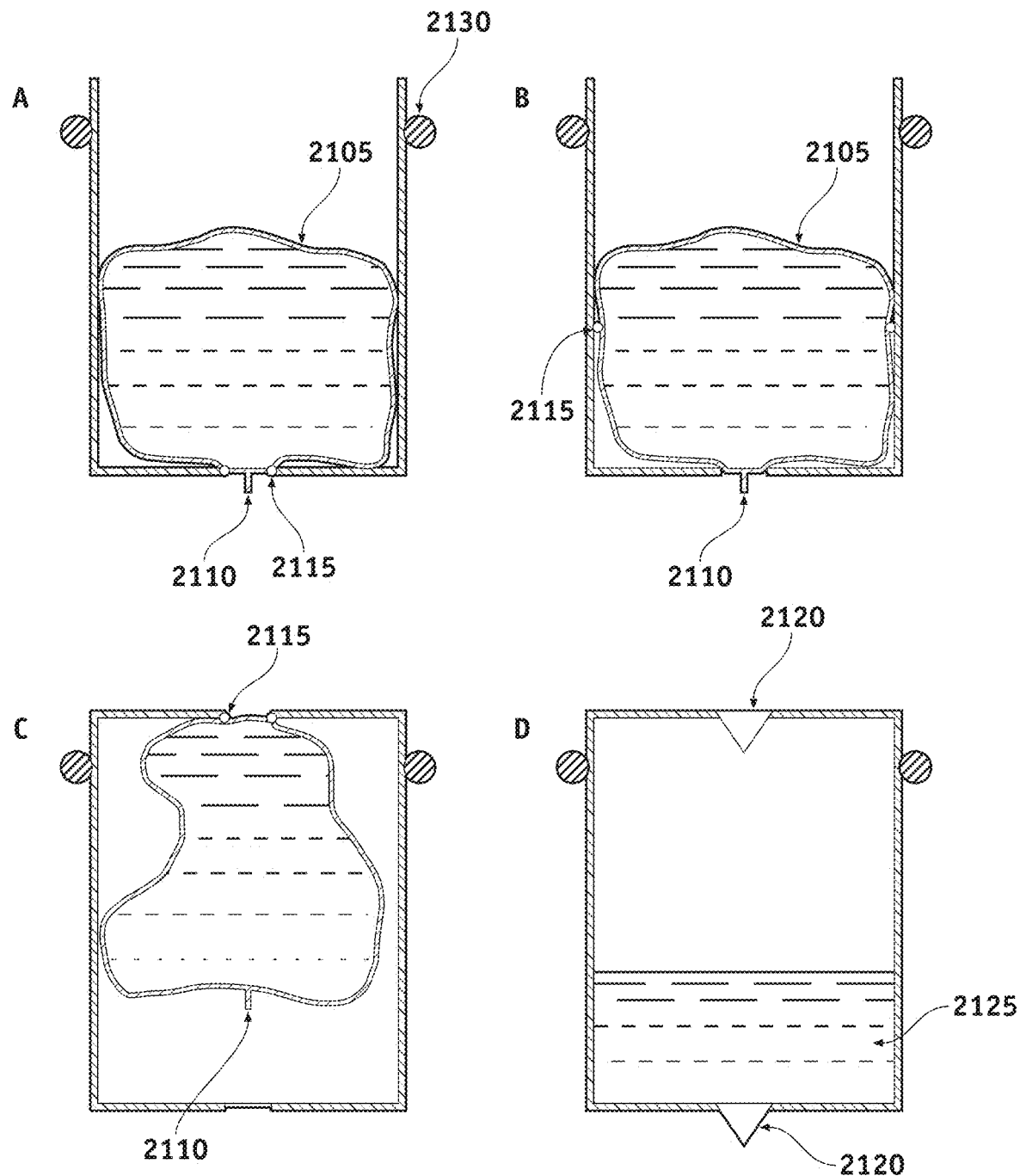
FIG. 21 illustrates exemplary alternatives to the pierceable membranes.

FIG. 21 illustrates exemplary alternatives to the pierceable membranes. FIG. 21 illustrates pressure activated pouches (2105), which can form an air tight seal at different locations (2115) of the chamber. The pouches can comprise a point (2110) designed to fail upon pressurization, and allow the fluid within the pouch to go through. The external seals (2130) of the chambers are also illustrated. In panel a of FIG. 21, the airtight seals are illustrated at the bottom opening of the chamber, while in panel b they are at the sides of the chamber, and in panel c at the top opening of the chamber. Panel d illustrates an alternative embodiment where the liquid (2125) within the chamber is contained by the use of pressure activated valves (2120).

With regard to the rotational layer: The rotational layer may have elastomeric surfaces on top on bottom for generating a seal with the top and bottom layers. To enhance the seal, the top and bottom layers may have ridges around each inlet and outlet. Alternatively, the elastomeric surface may be on the top and bottom layers and the ridges may be on the rotational layer.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

What is claimed is:

1. A device comprising:
   a plurality of chambers, each chamber of the plurality of chambers comprising a top opening, a bottom opening, and a seal;
   a lid configured to:
      seal the plurality of chambers by contacting the seal of each chamber of the plurality of chambers, and
      upon pushing of the lid towards the plurality of chambers, simultaneously pressurize each chamber of the plurality of chambers at a respective chamber pressure;
   a storage section comprising a plurality of receptacles; and
   a rotating section between the plurality of chambers and the storage section, the rotating section comprising a solid phase column, wherein the rotating section is configured to rotate to form, in sequence, a fluidic pathway between the solid phase column, the bottom opening of each chamber of the plurality of chambers, and a receptacle of the plurality of receptacles, thereby allowing flow of a fluid from the each chamber through the solid phase column into a receptacle of the plurality of receptacles, the fluid pressurized by the respective chamber pressure.

2. The device of claim 1, wherein:
   at least one chamber of the plurality of chambers comprises a pierceable membrane configured to contain a fluid within the at least one chamber,
   the lid comprises at least one piercer, and
   the lid is further configured to, upon pushing of the lid towards the plurality of chambers, pierce, by the at least one piercer, through the pierceable membrane of the at least one chamber.

3. The device of claim 2, wherein the plurality of chambers comprises: a first chamber to accept a sample, a second chamber containing a first wash buffer liquid, and a third chamber containing an elution buffer.

4. The device of claim 3, wherein the sample is a pre-lysed sample containing nucleic acids in a lysis buffer.

5. The device of claim 3, wherein the plurality of chambers further comprises a fourth chamber containing a second wash buffer liquid.

6. The device of claim 5, wherein the plurality of chambers further comprises a fifth chamber containing air.

7. The device of claim 6, wherein:
   the plurality of chambers further comprises a sixth chamber containing a negative control fluid,
   the rotating section further comprises an opening to form, upon rotation of the rotating section, a fluidic pathway between the sixth chamber and a negative control receptacle of the plurality of receptacles, and the plurality of receptacles comprises an elute receptacle.

8. The device of claim 7, wherein:

the at least one chamber comprising the pierceable membrane comprises the second chamber, the third chamber, the fourth chamber, and the sixth chamber, and the at least one piercer comprises a piercer for each of the second chamber, the third chamber, the fourth chamber, and the sixth chamber.

9. The device of claim 8, wherein:

the pierceable membrane of the second chamber, the third chamber, the fourth chamber, and the sixth chamber comprises a top pierceable membrane sealing a top end of the second chamber, the third chamber, the fourth chamber, and the sixth chamber, and a bottom pierceable membrane sealing a bottom end of the second chamber, the third chamber, the fourth chamber, and the sixth chamber, and the piercer for each of the second chamber, the third chamber, the fourth chamber, and the sixth chamber has a length extending from the top end to the bottom end of each of the second chamber, the third chamber, the fourth chamber, and the sixth chamber.

10. The device of claim 8, further comprising:

a first plate configured to attach to the storage section, the first plate comprising:
  a first fluidic channel having a first inlet and a first plurality of outlets; and
  a second fluidic channel having a second inlet and a second plurality of outlets; and a second plate comprising a first plurality of reaction wells and a second plurality of reaction wells, wherein:

the second plate is configured to rotate, relative to the first plate, between a first position and a second position, the first position forms a fluidic pathway between each reaction well of the first plurality of reaction wells and an outlet of the first plurality of outlets, and a fluidic pathway between each reaction well of the second plurality of reaction wells and an outlet of the second plurality of outlets, the second position fluidically isolates the first plurality of reaction wells from the first plurality of outlets, and the second plurality of reaction wells from the second plurality of outlets, and the storage section further comprises:

a first outlet in the elute receptacle, the first outlet configured to connect to the first inlet of the first plate; and a second outlet in the negative control receptacle, the second outlet configured to connect to the second inlet of the first plate.

11. The device of claim 10, further comprising a heater configured to control a temperature of the first plurality of reaction wells and of the second plurality of reaction wells, wherein the rotating section, the first plate, and the second plate each comprise a central opening configured to accept a motor shaft for motorized rotation of the rotating section, the first plate, and the second plate.

12. The device of claim 5, wherein the second wash buffer liquid comprises an alcohol with a chain length greater than 5.

13. The device of claim 1, wherein:

at least one chamber of the plurality of chambers comprises a pressure-activated membrane configured to contain a fluid within the at least one chamber, and the pressure-activated membrane is further configured to, upon pushing of the lid towards the plurality of chambers, burst, thereby releasing the fluid within the at least one chamber.

14. The device of claim 13, wherein the pressure-activated membrane has a failure point configured to burst upon pressurization.

15. The device of claim 1, wherein at least one chamber of the plurality of chambers comprises a pressure-activated valve configured to:

remain closed, thereby containing a fluid within the at least one chamber, and upon pressurization, open, thereby allowing flowing through of the fluid.

16. The device of claim 1, wherein the seal of the each chamber of the plurality of chambers is a rubber O-ring around an external surface of the each chamber of the plurality of chambers.

17. The device of claim 1, wherein the rotating section comprises a central opening configured to accept a motor shaft for motorized rotation of the rotating section.

18. The device of claim 1, wherein:

the respective chamber pressure of a first chamber of the plurality of chambers is independent from the respective chamber pressure of a second chamber of the plurality of chambers.

* * * * *

UNITED STATES PATENT AND TRADEMARK OFFICE
CERTIFICATE OF CORRECTION

Page 1 of 1

PATENT NO. : 11,149,265 B2
APPLICATION NO. : 16/130810
DATED : October 19, 2021
INVENTOR(S) : Rustem Ismagilov, Erik Jue and Daan Witters It is certified that error appears in the above-identified patent and that said Letters Patent is hereby corrected as shown below:

In the Specification

Under the section entitled "STATEMENT OF INTEREST" in Column 1, Lines 20-23 DELETE:
"This invention was made with government support under Grant No. HR0011-11-2-0006 awarded by DARPA. The government has certain rights in the invention."

And REPLACE with:
-- This invention was made with government support under Grant No. HR0011-11-2-0006 awarded by DARPA and under Grant No. W15QKN-16-9-1002 awarded by the Defense Threat Reduction Agency. The government has certain rights in the invention. --

Signed and Sealed this
Eighth Day of March, 2022

Drew Hirshfeld
*Performing the Functions and Duties of the
Under Secretary of Commerce for Intellectual Property and
Director of the United States Patent and Trademark Office*